US008623033B2

(12) United States Patent
Kubalak

(10) Patent No.: US 8,623,033 B2
(45) Date of Patent: Jan. 7, 2014

(54) SUTURE SYSTEM WITH CAPSULE EYELET PROVIDING MULTIPLE SUTURE TISSUE FIXATION

(75) Inventor: Thomas Kubalak, Wayzata, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/414,738

(22) Filed: Mar. 8, 2012

(65) Prior Publication Data

US 2013/0023906 A1    Jan. 24, 2013

(51) Int. Cl.
*A61B 17/62* (2006.01)

(52) U.S. Cl.
USPC .............................. 606/144; 606/139; 606/148

(58) Field of Classification Search
USPC ........................ 606/1, 139–148, 232; 112/169
See application file for complete search history.

(56) References Cited

U.S. PATENT DOCUMENTS

| | | | |
|---|---|---|---|
| 2,376,151 A | 5/1945 | Karle | |
| 2,376,152 A | 5/1945 | Karle | |
| 3,112,825 A | 12/1963 | Hammond et al. | |
| 3,376,973 A | 4/1968 | Granowitz et al. | |
| 3,545,608 A | 12/1970 | Berger et al. | |
| 3,638,653 A | 2/1972 | Berry | |
| 3,802,438 A * | 4/1974 | Wolvek | 606/232 |
| 3,964,468 A | 6/1976 | Schulz | |
| 4,440,171 A | 4/1984 | Nomoto et al. | |
| 4,699,271 A | 10/1987 | Lincoln et al. | |
| 5,027,433 A | 6/1991 | Menadier et al. | |
| 5,123,911 A | 6/1992 | Granger et al. | |
| 5,131,534 A | 7/1992 | Brown et al. | |
| 5,192,483 A | 3/1993 | Kilgrow et al. | |
| 5,201,743 A | 4/1993 | Haber et al. | |
| 5,224,948 A | 7/1993 | Abe et al. | |
| 5,271,495 A | 12/1993 | Alpern | |

(Continued)

FOREIGN PATENT DOCUMENTS

| | | |
|---|---|---|
| DE | 3223153 C1 | 8/1983 |
| EP | 1629780 | 3/2006 |

(Continued)

OTHER PUBLICATIONS

Office Action mailed on May 6, 2012 in U.S. Appl. No. 12/545,905.

(Continued)

*Primary Examiner* — Corrine M McDermott
*Assistant Examiner* — Mark Mashack
(74) *Attorney, Agent, or Firm* — Coloplast Corp., Coloplast A/S; Nick Baumann

(57) ABSTRACT

A suturing system includes a tool employed to pull at least two sutures through tissue. The tool includes a head having a proximal portion housing a needle movable through a needle exit port of the head and a distal end spaced apart from the proximal portion by a throat. The distal end of the head defines a cavity. A first suture is durably connected to a capsule that is sized for placement in the cavity. The capsule defines a through-hole sized for engagement with the needle and A second suture is removably insertable into the through-hole. The needle is movable from the proximal portion of the head across the throat to form a channel in tissue and to frictionally engage with the second suture and is retractable into the needle exit port to draw the capsule and the first and second sutures through the channel formed in the tissue.

12 Claims, 19 Drawing Sheets

(56) References Cited

U.S. PATENT DOCUMENTS

| | | | |
|---|---|---|---|
| 5,290,300 A | 3/1994 | Cosgrove et al. | |
| 5,306,281 A | 4/1994 | Beurrier | |
| 5,307,924 A | 5/1994 | Manosalva et al. | |
| 5,320,629 A | 6/1994 | Noda et al. | |
| 5,336,229 A | 8/1994 | Noda | |
| 5,364,407 A * | 11/1994 | Poll | 606/139 |
| 5,364,408 A | 11/1994 | Gordon | |
| 5,391,174 A | 2/1995 | Weston | |
| 5,392,903 A | 2/1995 | Sinn | |
| 5,431,666 A | 7/1995 | Sauer et al. | |
| 5,458,609 A | 10/1995 | Gordon et al. | |
| 5,472,081 A | 12/1995 | Kilgrow et al. | |
| 5,478,344 A | 12/1995 | Stone et al. | |
| 5,478,345 A | 12/1995 | Stone et al. | |
| 5,496,336 A | 3/1996 | Cosgrove et al. | |
| 5,540,704 A | 7/1996 | Gordon et al. | |
| 5,562,686 A * | 10/1996 | Sauer et al. | 606/144 |
| 5,568,865 A | 10/1996 | Mase et al. | |
| 5,571,119 A | 11/1996 | Atala | |
| 5,575,800 A | 11/1996 | Gordon | |
| 5,578,044 A | 11/1996 | Gordon et al. | |
| 5,630,825 A | 5/1997 | de la Torre et al. | |
| 5,662,664 A | 9/1997 | Gordon et al. | |
| 5,683,402 A | 11/1997 | Cosgrove et al. | |
| 5,700,272 A | 12/1997 | Gordon et al. | |
| 5,704,469 A | 1/1998 | Daniele et al. | |
| 5,713,910 A | 2/1998 | Gordon et al. | |
| 5,728,113 A | 3/1998 | Sherts | |
| 5,728,135 A | 3/1998 | Bregen et al. | |
| 5,741,277 A | 4/1998 | Gordon et al. | |
| 5,755,729 A | 5/1998 | de la Torre et al. | |
| 5,792,153 A * | 8/1998 | Swain et al. | 606/144 |
| 5,918,733 A | 7/1999 | Cerwin et al. | |
| 5,919,199 A | 7/1999 | Kelly et al. | |
| 5,931,844 A * | 8/1999 | Thompson et al. | 606/144 |
| 5,938,668 A | 8/1999 | Scirica et al. | |
| 5,980,538 A | 11/1999 | Fuchs et al. | |
| 6,048,351 A | 4/2000 | Gordon et al. | |
| 6,071,289 A | 6/2000 | Stefanchik et al. | |
| 6,102,920 A | 8/2000 | Sullivan et al. | |
| 6,117,144 A | 9/2000 | Nobles et al. | |
| 6,283,993 B1 | 9/2001 | Cosgrove et al. | |
| 6,332,888 B1 | 12/2001 | Levy et al. | |
| 6,346,111 B1 | 2/2002 | Gordon et al. | |
| 6,475,135 B1 | 11/2002 | Levy | |
| 6,478,791 B1 | 11/2002 | Carter et al. | |
| 6,551,330 B1 | 4/2003 | Bain et al. | |
| 6,554,845 B1 | 4/2003 | Fleenor et al. | |
| 6,592,625 B2 | 7/2003 | Cauthen | |
| 6,638,286 B1 | 10/2003 | Burbank et al. | |
| 6,719,764 B1 | 4/2004 | Gellman et al. | |
| 6,802,860 B2 | 10/2004 | Cosgrove et al. | |
| 6,893,448 B2 | 5/2005 | O'Quinn et al. | |
| 6,921,408 B2 | 7/2005 | Sauer | |
| 6,936,054 B2 | 8/2005 | Chu | |
| 6,984,247 B2 | 1/2006 | Cauthen | |
| 6,997,932 B2 | 2/2006 | Dreyfuss et al. | |
| 7,004,970 B2 | 2/2006 | Cauthen, III et al. | |
| 7,033,370 B2 | 4/2006 | Gordon et al. | |
| 7,041,111 B2 | 5/2006 | Chu | |
| 7,048,749 B2 | 5/2006 | Kortenbach et al. | |
| 7,052,516 B2 | 5/2006 | Cauthen, III et al. | |
| 7,060,077 B2 | 6/2006 | Gordon et al. | |
| 7,090,690 B2 * | 8/2006 | Foerster et al. | 606/232 |
| 7,118,583 B2 | 10/2006 | O'Quinn et al. | |
| 7,122,039 B2 | 10/2006 | Chu | |
| 7,122,040 B2 | 10/2006 | Hill et al. | |
| 7,189,235 B2 | 3/2007 | Cauthen | |
| 7,232,448 B2 | 6/2007 | Battles et al. | |
| 7,442,198 B2 | 10/2008 | Gellman et al. | |
| 7,445,626 B2 * | 11/2008 | Songer et al. | 606/224 |
| 8,226,666 B2 * | 7/2012 | Zarbatany et al. | 606/139 |
| 8,257,368 B2 * | 9/2012 | McIntosh | 606/144 |
| 2002/0143234 A1 * | 10/2002 | LoVuolo | 600/30 |
| 2002/0193810 A1 | 12/2002 | Hill et al. | |
| 2003/0023250 A1 | 1/2003 | Watschke et al. | |
| 2003/0093093 A1 | 5/2003 | Modesitt et al. | |
| 2003/0149447 A1 * | 8/2003 | Morency et al. | 606/228 |
| 2003/0233108 A1 | 12/2003 | Gellman et al. | |
| 2003/0236549 A1 | 12/2003 | Bonadio et al. | |
| 2004/0097968 A1 * | 5/2004 | Shikhman et al. | 606/139 |
| 2004/0111114 A1 * | 6/2004 | Shikhman et al. | 606/213 |
| 2004/0181243 A1 | 9/2004 | Chu et al. | |
| 2004/0186340 A1 * | 9/2004 | Reed et al. | 600/7 |
| 2004/0236356 A1 | 11/2004 | Rioux et al. | |
| 2005/0033319 A1 * | 2/2005 | Gambale et al. | 606/139 |
| 2005/0143762 A1 * | 6/2005 | Paraschac et al. | 606/148 |
| 2005/0154403 A1 | 7/2005 | Sauer et al. | |
| 2005/0222589 A1 | 10/2005 | Chu | |
| 2005/0228405 A1 | 10/2005 | Maruyama et al. | |
| 2006/0041263 A1 | 2/2006 | Chu et al. | |
| 2006/0047289 A1 * | 3/2006 | Fogel | 606/139 |
| 2006/0069397 A1 * | 3/2006 | Nobles et al. | 606/144 |
| 2006/0224184 A1 | 10/2006 | Stefanchik et al. | |
| 2006/0293699 A1 | 12/2006 | Robertson | |
| 2007/0198035 A1 | 8/2007 | Threlkeld | |
| 2007/0225815 A1 | 9/2007 | Keith et al. | |
| 2007/0239280 A1 | 10/2007 | Keith et al. | |
| 2007/0255296 A1 | 11/2007 | Sauer | |
| 2007/0270885 A1 | 11/2007 | Weinert et al. | |
| 2007/0270890 A1 | 11/2007 | Miller | |
| 2008/0045976 A1 * | 2/2008 | Gibbons et al. | 606/139 |
| 2008/0051833 A1 | 2/2008 | Gramuglia et al. | |
| 2008/0071295 A1 | 3/2008 | Baxter et al. | |
| 2008/0077162 A1 | 3/2008 | Domingo | |
| 2008/0082105 A1 | 4/2008 | Chu | |
| 2008/0091220 A1 | 4/2008 | Chu | |
| 2008/0109015 A1 | 5/2008 | Chu et al. | |
| 2008/0269782 A1 | 10/2008 | Stefanchik et al. | |
| 2009/0005793 A1 | 1/2009 | Pantages et al. | |
| 2009/0069824 A1 | 3/2009 | Chu | |
| 2010/0084294 A1 | 4/2010 | Kirsch et al. | |
| 2010/0130990 A1 * | 5/2010 | Saliman | 606/145 |
| 2010/0331623 A1 * | 12/2010 | Sauer et al. | 600/106 |
| 2011/0022063 A1 * | 1/2011 | McClurg et al. | 606/145 |
| 2011/0042245 A1 | 2/2011 | McClurg et al. | |
| 2011/0046642 A1 | 2/2011 | McClurg et al. | |
| 2011/0046644 A1 | 2/2011 | McClurg et al. | |
| 2011/0046645 A1 | 2/2011 | McClurg et al. | |
| 2011/0054249 A1 | 3/2011 | Narthasilpa et al. | |
| 2011/0092991 A1 | 4/2011 | Gaynor et al. | |
| 2011/0118758 A1 * | 5/2011 | Sauer | 606/144 |
| 2011/0130773 A1 | 6/2011 | Saliman et al. | |
| 2011/0196387 A1 * | 8/2011 | Pantages et al. | 606/139 |
| 2011/0224698 A1 * | 9/2011 | Deitch et al. | 606/144 |
| 2011/0270280 A1 * | 11/2011 | Saliman | 606/145 |
| 2012/0221022 A1 * | 8/2012 | Devens et al. | 606/144 |
| 2012/0316582 A1 * | 12/2012 | Nobles et al. | 606/148 |
| 2012/0323263 A1 * | 12/2012 | McClurg et al. | 606/144 |

FOREIGN PATENT DOCUMENTS

| | | |
|---|---|---|
| FR | 1238904 | 7/1960 |
| FR | 2320253 | 3/1977 |
| GB | 2368575 | 5/2002 |
| WO | 9922648 | 5/1999 |
| WO | 2005037152 | 4/2005 |
| WO | 2005070305 A1 | 8/2005 |
| WO | 2005110241 | 11/2005 |
| WO | 2008147555 A2 | 12/2008 |
| WO | 2009005527 | 1/2009 |

OTHER PUBLICATIONS

Office Action mailed on Apr. 9, 2012 in U.S. Appl. No. 12/833,006.
Office Action mailed on Jan. 6, 2012 in U.S. Appl. No. 12/813,517.
Office Action mailed on Dec. 21, 2011 in U.S. Appl. No. 12/545,905.

* cited by examiner

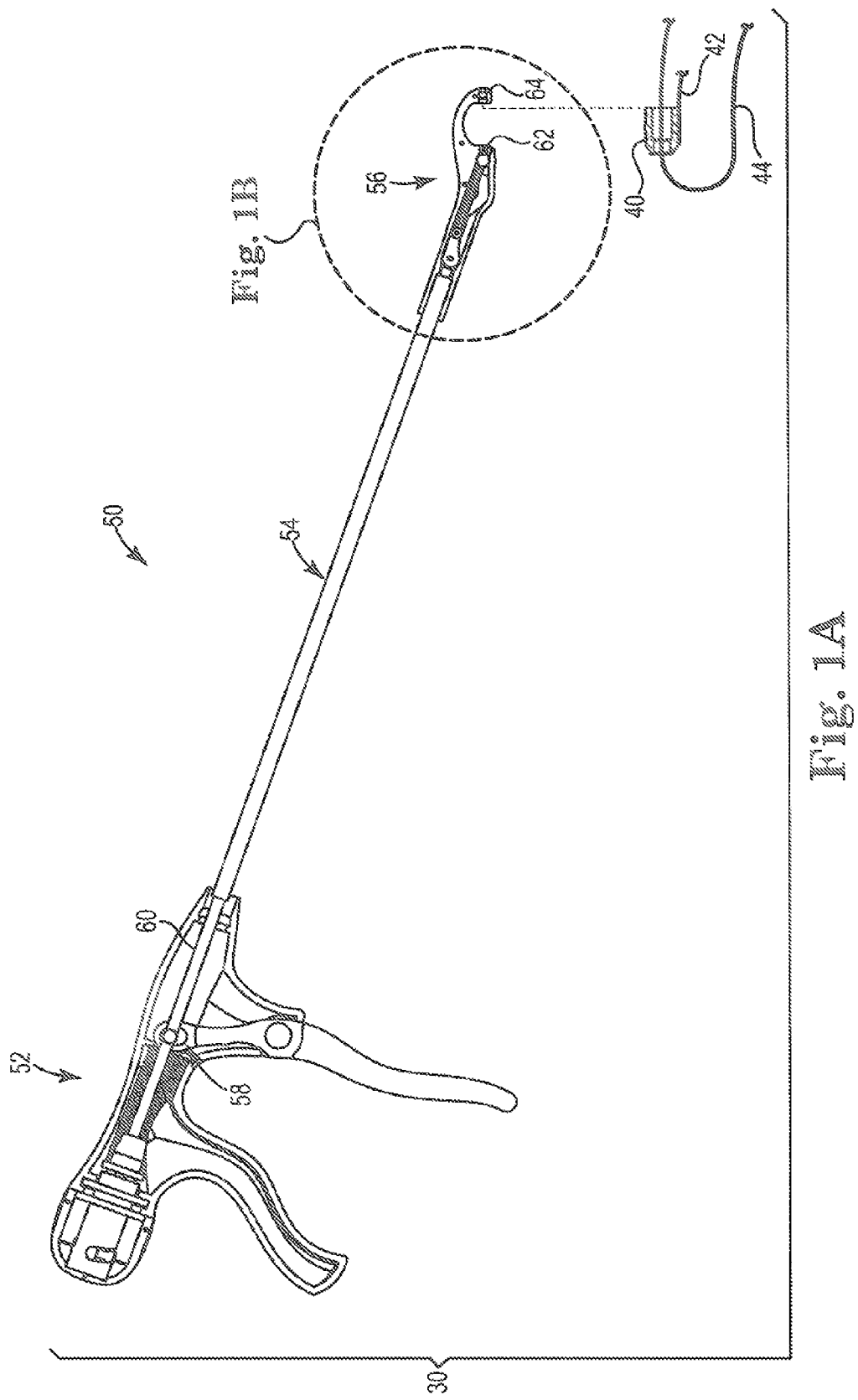

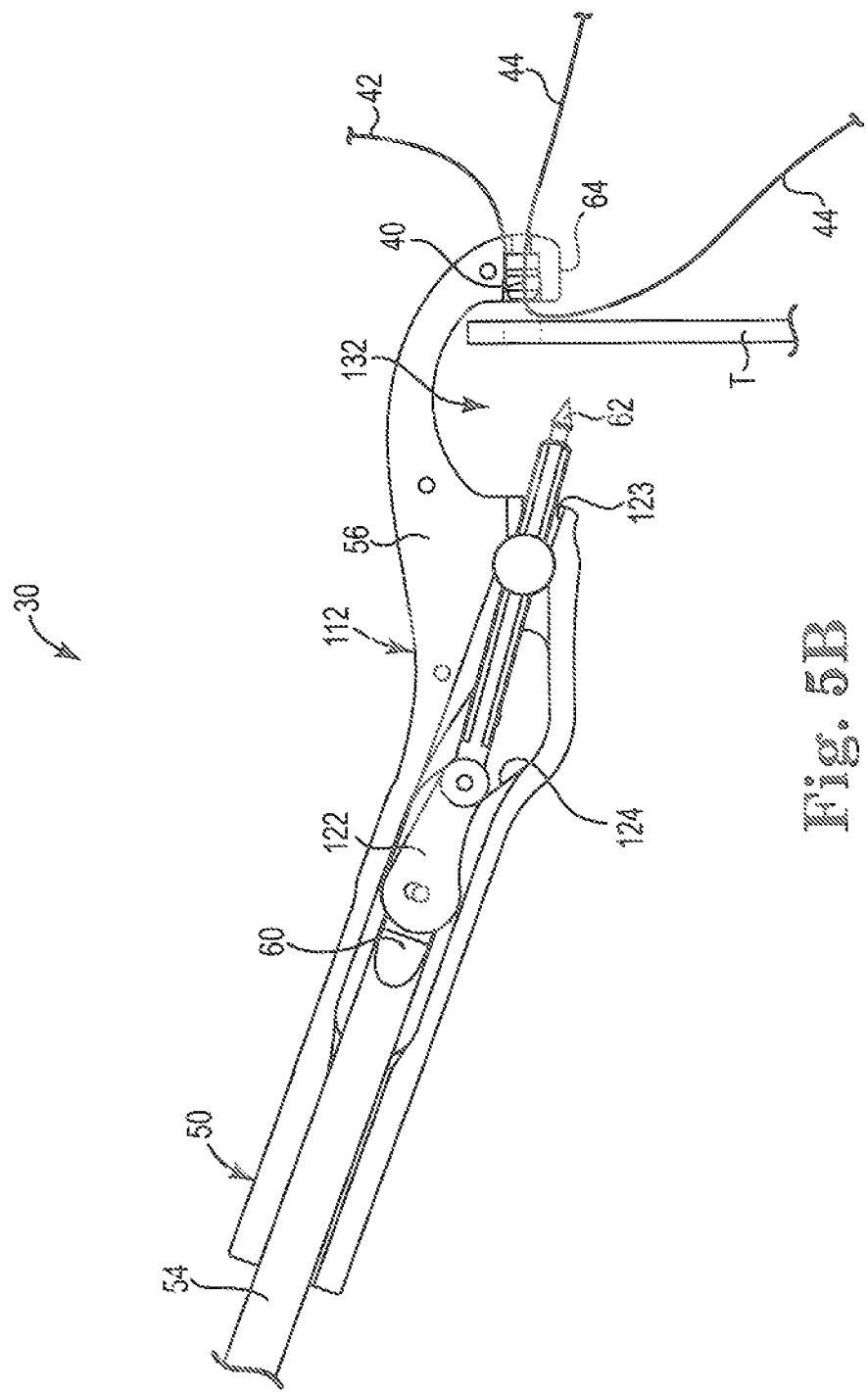

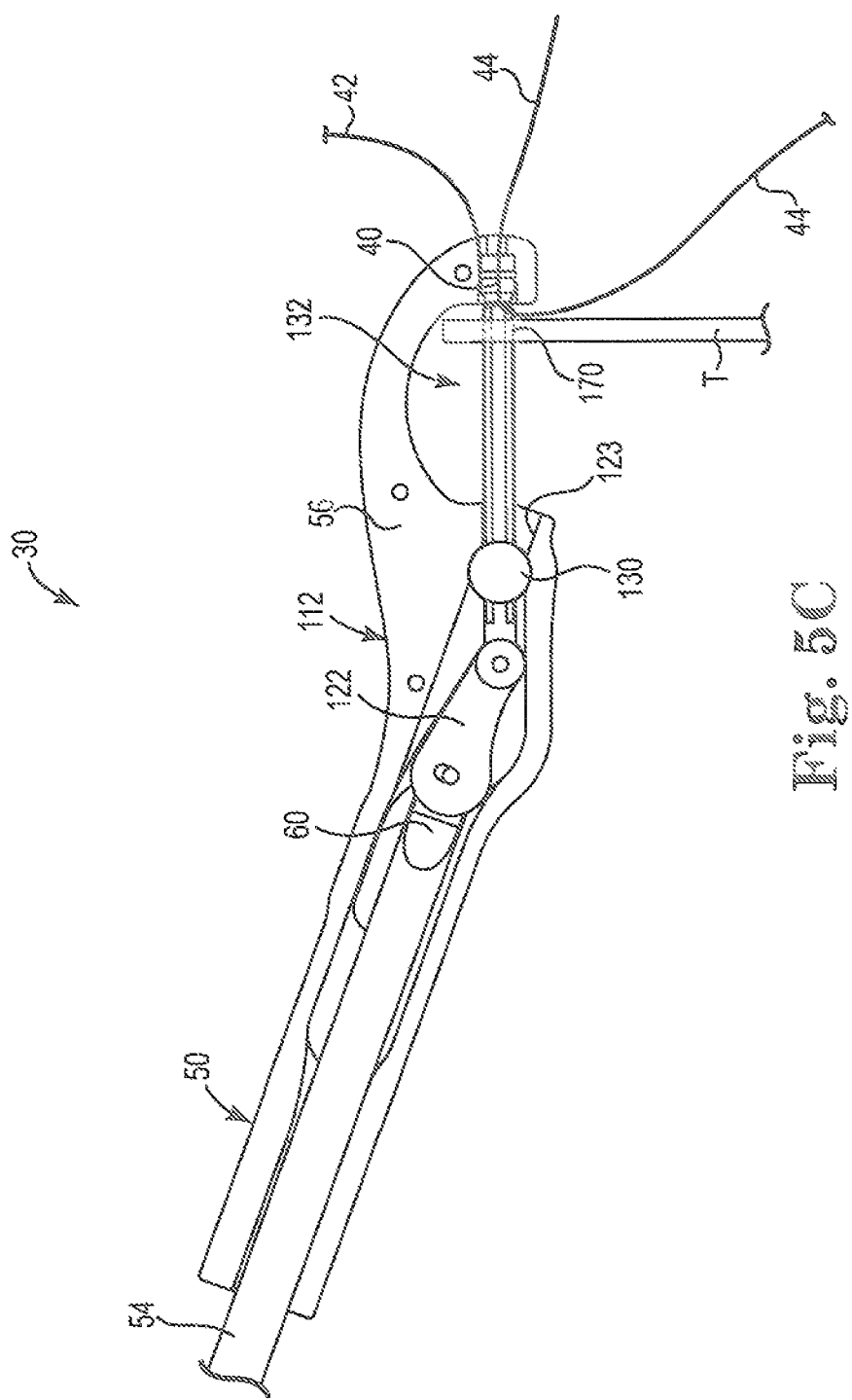

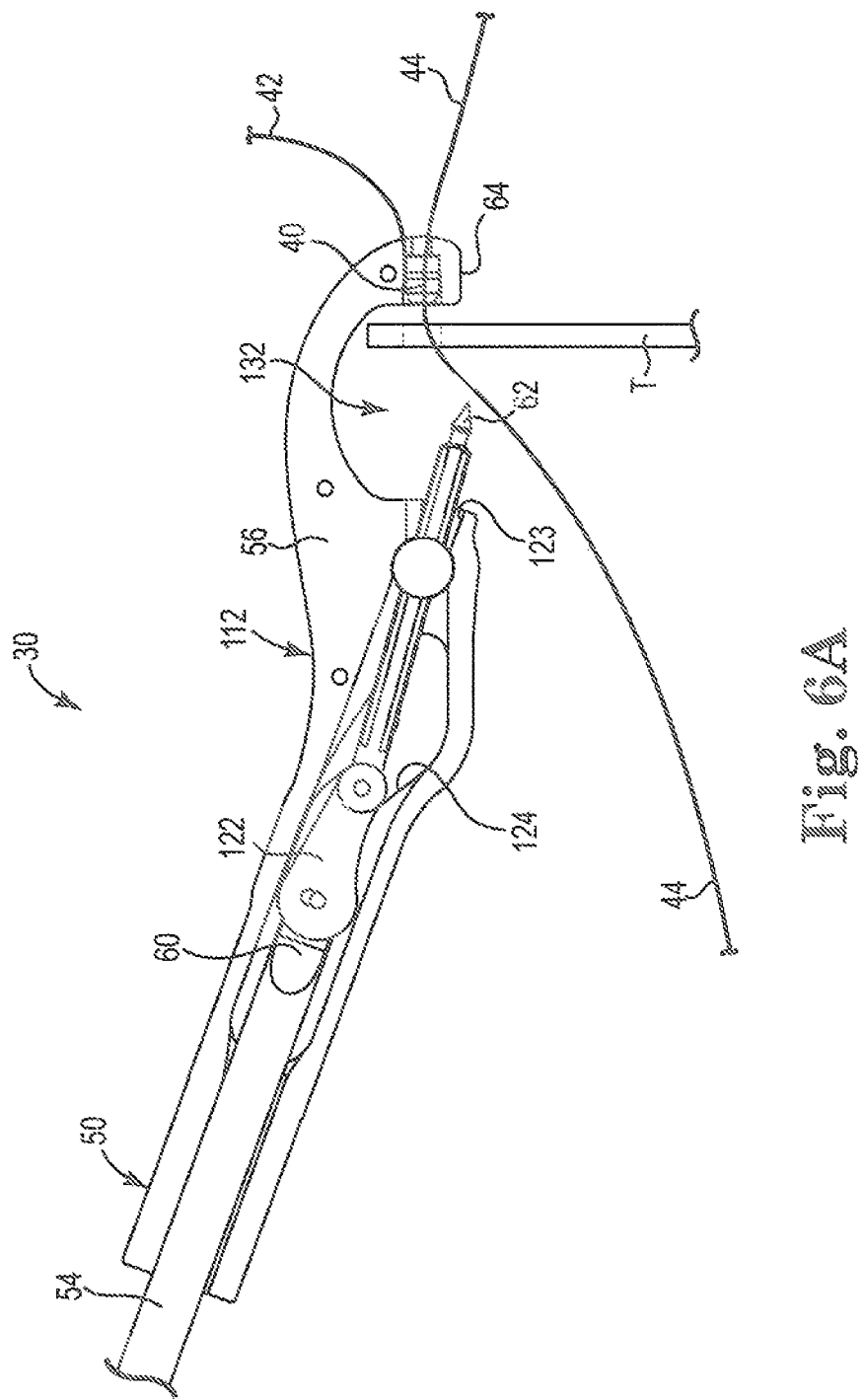

SUTURE SYSTEM WITH CAPSULE EYELET PROVIDING MULTIPLE SUTURE TISSUE FIXATION

BACKGROUND

Intracorporeal suturing of tissue during surgery presents challenges to the surgeon in that the surgeon is called upon to manipulate suturing instruments in blind passages accessed through small incisions formed in the patient's body. In some cases, the surgeon digitally palpates a desired location for placement of the suture and is unable to see the suture site.

Improved suturing instruments and improved methods of delivering sutures would be welcomed by the surgical staff.

SUMMARY

One aspect provides a suturing system including a tool provided to draw multiple sutures through a channel formed in tissue. The system includes a tool having a head including a proximal portion housing a needle movable through a needle exit port of the head and a distal end spaced apart from the proximal portion by a throat. The distal end of the head is radially offset from the longitudinal axis and defines a cavity. A first suture is attached to a capsule, and the capsule is sized for placement in the cavity. The capsule defines a through-hole sized for engagement with the needle. A second suture is configured to be threaded through the through-hole of the capsule. The needle is movable from the proximal portion of the head across the throat to form a channel in tissue, and is retractable into the needle exit port to draw the capsule and the first and second sutures through the channel formed in the tissue to place multiple lengths of suture in the tissue.

One aspect provides a method of suturing tissue that includes driving a needle from a tool through tissue to form a channel in the tissue; inserting the needle into a capsule that is connected to a first length of suture attached to the capsule; engaging the needle with a second length of suture that is inserted through the capsule; and pulling both the first length of suture and the second length of suture through the channel formed in the tissue.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1A is a side sectional view of one embodiment of a suturing system including a suturing capsule insertable into a head of a tool.

FIG. 5B is a schematic sectional view of the needle partially extending from an exit port of the head.

FIG. 5C is a schematic sectional view of the needle having formed a channel in the tissue and engaged with the capsule.

FIGS. 6A-6D are schematic views of embodiments of the system employed to throw multiple suture lines through tissue including a sacrificial suture line and a desired alternate suture line.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this specification, shunt means to move an object away from a first axis to another axis that is different from the first axis. For example, in one embodiment a suturing device includes a needle that is moved in a first direction (e.g., along a longitudinal axis) and is subsequently moved in a second direction different from the first direction (i.e., away from the longitudinal axis); thus the needle is shunted away from a longitudinal axis when deployed from the device.

In this specification, end means endmost and end portion means that segment that is adjacent to and extends from the end. For example, a proximal end is that end location of a handheld instrument that is nearest a user, and a proximal end portion is that segment (e.g., a handle of the handheld instrument) that is adjacent to and extends distally away from the proximal end.

In this specification, durably connected means that a suture attached to a capsule is connected in a manner that the force to remove the suture from the capsule is greater than the tensile force of the suture ("strain at break") such that the suture will fracture or break before the suture will release from the capsule.

Embodiments provide a system and a method of placing multiple suture lines through tissue. One or more of the suture lines may be discarded leaving one or more suture lines of a desired composition placed in the tissue. For example, embodiments provide a system for placing a body-absorbable or bioabsorbable suture into tissue.

Figure 1B:
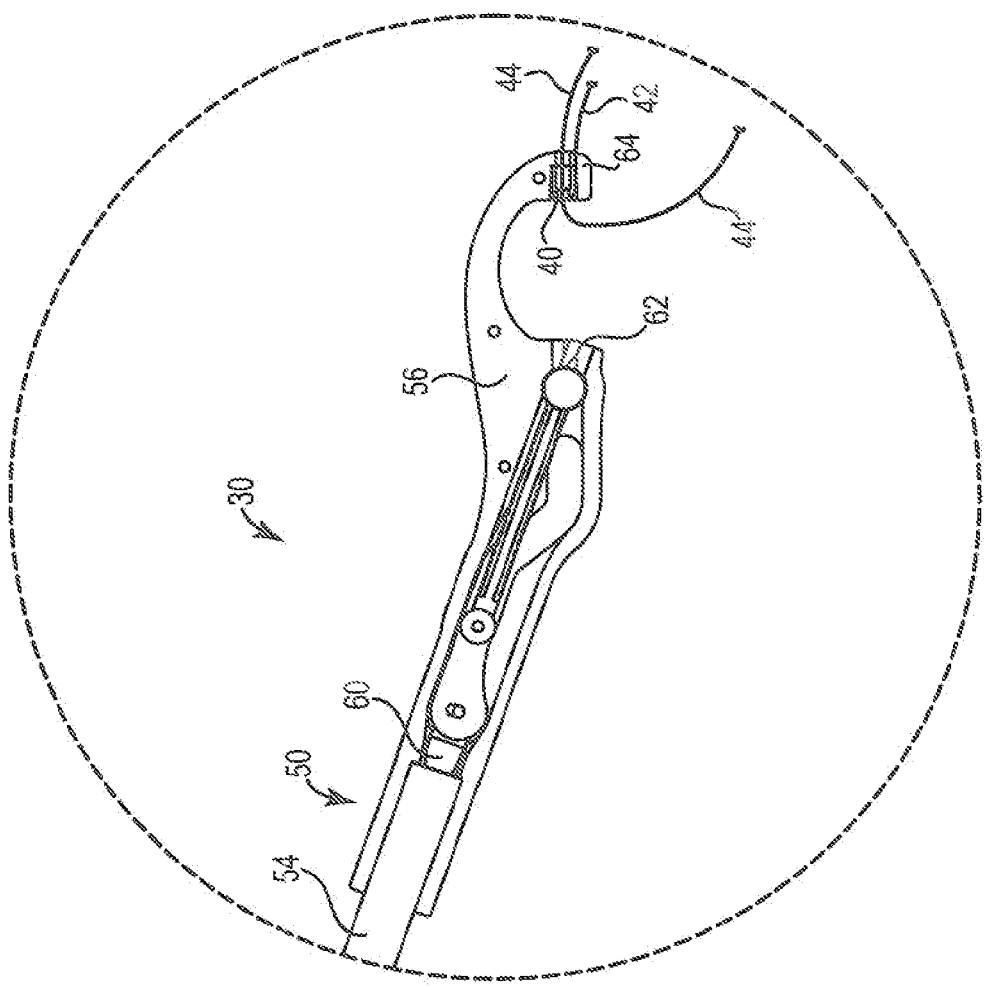
FIG. 1B is a side sectional view of one embodiment of the head of the tool illustrated in FIG. 1 engaged with the suturing capsule and multiple lines of suture.

FIG. 1A and FIG. 1B are side sectional views in partial cross-section of one embodiment of a suturing system 30 useful for placing multiple lines of suture through tissue. The suturing system 30 includes a capsule 40 connected to a first suture 42, a second suture 44 inserted through the capsule 40, and a tool 50 that is operable to place the sutures 42, 44 through the tissue. FIG. 1A illustrates the suture 42 durably connected to the capsule 40 and the second suture 44 inserted through a hole formed in the capsule 40. FIG. 1B is a side sectional view of the capsule 40 inserted into the head 56 of the tool 50.

Although two sutures 42 and 44 are illustrated it is to be understood that the system 30 is operable to place more than two sutures in tissue. For example, multiple second sutures 44 could be sutured into tissue by the system 30. The capsule 40 and the sutures 42, 44 are described below.

The tool 50 includes a handle 52, a shaft 54 coupled to handle 52, and a head 56 coupled to shaft 54. The handle 52 thus defines a proximal end of tool 50 and is nearest a user of tool 50.

In one embodiment, the handle 52 includes an actuator 58 communicating with a rod 60 that is disposed within the shaft 54. When the actuator 58 is activated, the rod 60 moves through the shaft 54 to extend a needle 62 stored within a proximal end portion of the head 56 axially outward through the tissue and toward a distal end 64 of the head 56. Thus, the needle 62 moves away from the user (who is holding handle 52 at the proximal end of tool 50) toward the distal end 64 of the tool 50.

In one embodiment, the capsule 40 is retained within the distal end 64, and the needle 62 is shaped to frictionally engage and mate with the capsule 40 and the second suture 44 inserted through the capsule 40, remove the capsule 40 and the sutures 42, 44 from the distal end 64, and retract the capsule 40 into the proximal end portion of the head 56. In this manner, the sutures 42, 44 are towed behind the capsule 40 by the needle 62 and "thrown" through the tissue. Embodiments described below include a guide pin located within the head 56 that is configured to disengage the capsule from the needle 62 after the sutures 42, 44 are placed in the tissue.

The tool 50 is suited for the intracorporeal suturing of tissue during surgery, and in one embodiment is provided as a sterile disposable surgical instrument that is discarded after the surgical procedure. To this end, the components of the tool 50 are selected to be compatible with sterilization techniques.

In one embodiment, the tool 50 is suited for suturing tissue inside the pelvis and is sized to access the pelvis by a blind passage through an incision. For example, in one embodiment the head 56 is inserted through a vaginal incision or a perineal incision or other suitable incision into the pelvis and the sutures 42, 44 are placed into tissue inside the pelvis. A portion of the sutures 42, 44 are drawn through the incision to a location outside of the pelvis. In one embodiment, each of the first and second sutures 42, 44 have a length that is greater than 2 inches, preferably the sutures 42, 44 have a length that is greater than 4 inches, and more preferably the sutures 42, 44 have a length that is greater than 8 inches. In one embodiment, at least the second suture 44 has a length between 2-36 inches long and is suited for trailing out of the pelvis to provide a pathway for placement of support material into the pelvis.

In one embodiment, the first suture 42 is a sacrificial suture that is subsequently severed and removed away from the second suture 44. A support fabric suitable for treating stress urinary incontinence or pelvic organ prolapse is attachable to the second suture 44 and delivered to the tissue inside of the pelvis to treat stress urinary incontinence or pelvic organ prolapse or support other organs inside the pelvis.

In one embodiment, the first suture 42 is a sacrificial polypropylene suture that is discarded after delivering the second suture 44 through tissue. The second suture 44 is suitably selected by the surgeon as a bioabsorbable, body absorbable, degradable, metal, or other suture. The second suture 44 can be the same as or different from the first suture 42.

Suitable second sutures 44 are available from Teleflex, Manfield, Mass. or CP Medical, Portland, Oreg. Other suitable second sutures 44 are available from Ethicon™, a J&J Company located in Somerville, N.J., and include bioabsorbable and other sutures such as Monocryl™ (polyglycaprone 25) sutures, coated Vicryl™ (polyglactin 910) sutures, Ethicon Plus™ Sutures, or polydioxanone sutures as examples. Other examples of suitable bioabsorbable/body-absorbable sutures are the Caprosyn™, Polysorb™, and Biosyn™ absorbable sutures available from Covidien, Norwalk, Conn.

Figure 2:
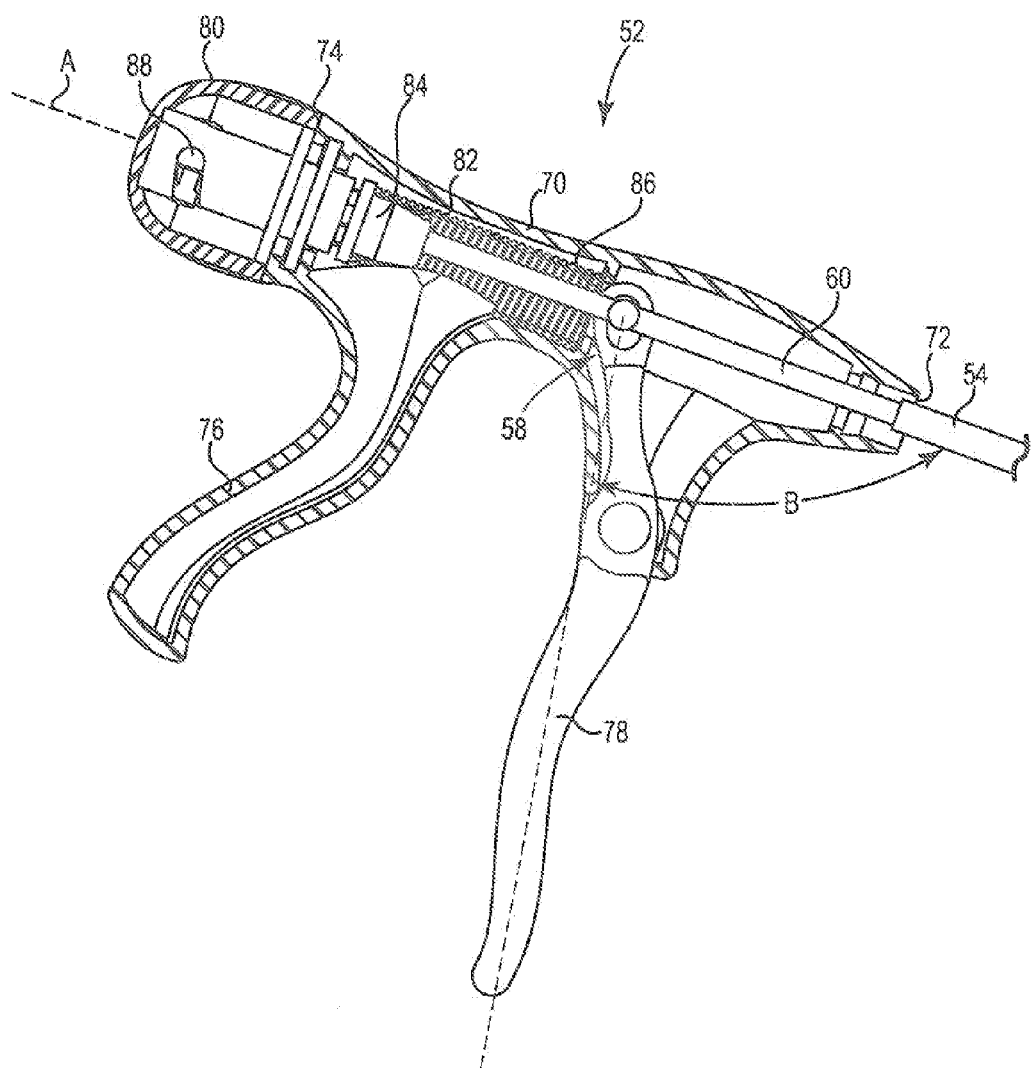
FIG. 2 is a cross-sectional view of one embodiment of a handle of the tool illustrated in FIG. 1.

FIG. 2 is a cross-sectional view of one embodiment of the handle 52. The handle 52 is aligned with a major longitudinal axis A and includes a body 70 extending between a distal end 72 and a proximal end 74, a thumb brace 76 extending laterally from body 70, a trigger 78 spaced apart from the thumb brace 76, and a knob 80 coupled to the proximal end 74.

In one embodiment, the body 70 is fabricated from plastic, for example via injection molding. Suitable plastic materials for the fabrication of the body 70, the brace 76, and the knob 80 include, as examples, polycarbonate, polyethylene, acrylonitrile butadiene styrene, acrylic, or nylon. In one embodiment, the brace 76 is integrally molded with a clamshell-style of body 70 and these two components are joined together to retain the trigger 78 and the knob 80. The trigger 78 is formed to have sufficient strength to resist bending when activated by the human hand. Suitable materials for forming the trigger 78 include metal such as aluminum or plastics such as polyetherimide or poly-ether-ether-ketone.

The shaft 54 is coupled to the distal end 72 of the body 70, and the rod 60 is disposed within the shaft 54 and coupled to the trigger 78. In one embodiment, the actuator 58 includes the trigger 78 attached to the rod 60 and a spring 82 disposed within a spring pusher 84 and biased against and an internal rib 86. The trigger 78 is movable toward the thumb brace 76 to move the rod 60 in a distal direction longitudinally within the shaft 54, which compresses the spring 82. When the trigger 78 is released, the spring 82 extends to push the spring pusher 84 proximally, which retracts or returns the rod 60 toward the proximal end 74. The trigger 78 is spaced apart from the thumb brace 76 by a distance of approximately 4-12 cm to enable the fingers of the user to comfortably activate the trigger 78. The trigger 78 is disposed at an angle B relative to the longitudinal axis A of the body 70, and in an exemplary embodiment the angle B is between 70-110 degrees such that the trigger 78 is approximately orthogonal to longitudinal axis A.

The actuator 58 is configured to move the rod 60 forward in a distal direction and rearward in a proximal direction within the shaft 54. In one embodiment, it is desirable to move the rod 60 rearward an additional distance to disengage the capsule 40 from the needle 62 (FIG. 1B). To facilitate this, the rod 60 includes an insert (not shown) that communicates through the spring pusher 84 and is captured in the window 88. When the knob 80 is turned, the spring pusher 84 turns and the insert attached to the rod 60 is retracted back in a proximal direction due to the angle of the window 88, which retracts the rod 60 an additional distance into the body 70. For example, in one embodiment the knob 80 is configured such that a 180 degree clockwise turn of the knob 80 relative to the end 74 draws the rod 60 an additional distance of about 2 mm into the body 70. Although the knob 80 is configured to retract the rod 60 further into the body 70 via a turning motion, other mechanisms such as levers or draw bars for retracting the rod 60 incrementally rearward are also acceptable.

One suitable embodiment of a shaft 54 includes a substantially rigid metal annular tube extending between a proximal end that is attachable to the handle 52 (FIG. 1A) and a distal end that is attachable to the head 56. Another embodiment of the shaft 54 includes a distal end portion that is malleable, or bendable/flexible and so configured to bend laterally relative to the handle 52 to enable the surgeon to selectively direct the head 56 to a desired location. In one embodiment, the shaft 54 is formed as a thin-walled tube with a first section formed of a first material and a second section formed of a different second material. In an exemplary embodiment, the first section is formed of 6,000 series aluminum and the second section 98 is formed of 3000 series aluminum, with these two metal sections joined together by crimp/weld. The 6000 series aluminum is selected to have a shear modulus of a sufficient value to preclude the user from bending the first section as the tool 50 is manipulated. For example, in one embodiment the shear modulus of the first section is approximately 30 $GN/m^2$. The 3000 series aluminum is selected to have a shear modulus of a sufficient value to enable a user to bend the second section with their hands, which enables the user to shape and guide the second section (which is attached to the head 56) in controlling and guiding the placement of sutures with the head 56. For example, in one embodiment the shear modulus of the second section is approximately 10 $GN/m^2$.

In one embodiment, the rod 60 is formed of a coiled stainless steel spring and includes a polyethylene jacket, as one example, disposed around the coiled spring. In one embodiment, only a leading section of the rod 60 is formed of coiled springs, where the leading section corresponds to the flexible second section of the shaft 54, such that the rod 60 is provided with substantially the same lateral flexibility as the shaft 54. In one embodiment, the rod 60 is formed of aluminum and configured to have similar flexibility as the shaft 54.

Figure 3:
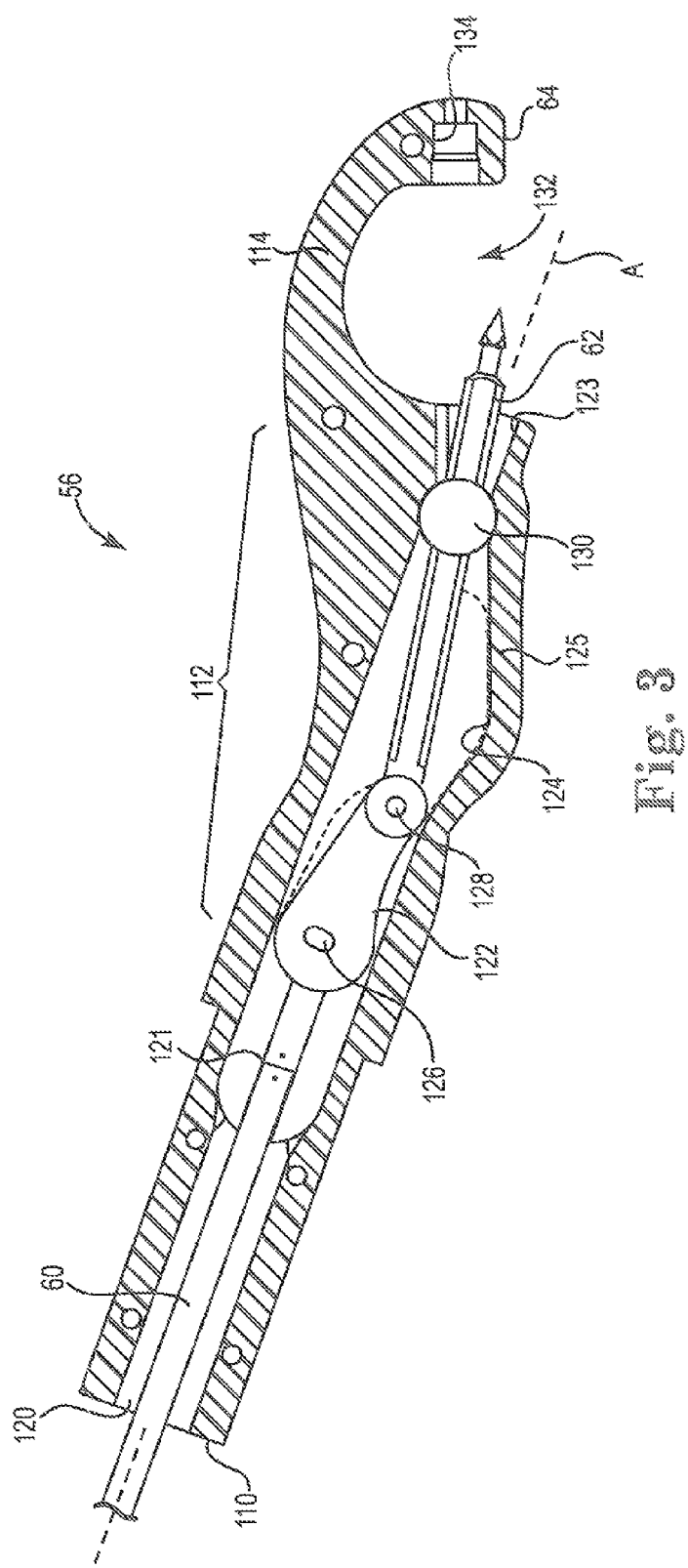
FIG. 3 is a cross-sectional view of one embodiment of the head of the tool illustrated in FIG. 1 including a movable needle.

FIG. 3 is a cross-sectional view of the head 56. In one embodiment, the head 56 is formed of two mating clamshell components, and the view of FIG. 3 is taken with one half of the clamshell structure removed so that the internal features of the head 56 are visible. The head 56 is molded from plastic, for example from a polyether imide plastic sold under the trademark Ultem, or from glass-filled polyether imide plastics also sold under the trademark Ultem.

In one embodiment, the head 56 includes a proximal end 110 opposite the distal end 64, a proximal end portion 112 extending from the proximal end 110, and a neck 114 that extends between the proximal end portion 112 and the distal end 64. The head 56 is attachable to the shaft 54, and in one embodiment includes an opening 120 sized to receive the shaft 54 such that the rod 60 extends into the proximal end portion 112 and couples with a link 122 that is attached to the needle 62. In one embodiment, the distal end 64 is not aligned with, but is rather offset radially from the longitudinal axis A, to more comfortably position the shaft 54 for manipulation by the surgeon as to head 56 is engaged with the tissue.

In one embodiment, a clevis pin 121 connects a proximal end of the link 122 to the rod 60 and a distal end of the link 122 is coupled to the needle 62. Movement of the rod 60 moves the link 122, which moves the needle 62 into and out of a needle exit port 123 formed in the proximal end portion 112. In one embodiment, a trace 124 that is formed on an interior surface 125 of the proximal end portion 112 of the head 56, and the link 122 is configured to translate and rotate within the trace 124 to translate the needle 62 along axis A and pitch the needle up/down relative to the axis A. For example, in one embodiment the link 122 includes a first pin 126 that couples with the clevis 121 and a second pin 128 that couples with the needle 62. Axial movement of the rod 60 translates to axial movement of the link 122 and the needle 62, and the link 122 rotates about the pins 126, 128 to shunt a path of the needle 62 off of the axis A.

The link 122 is thus configured to translate within the trace 124 to move the needle 62 in/out relative to the needle exit port 123, and rotate relative to a pins 126, 128 to direct movement of the needle 62 up/down relative to the longitudinal axis A. In one embodiment, the proximal end portion 112 includes a guide pin 130 that defines a bore sized to receive a needle 62. The needle 62 is configured to slide through the bore formed in the guide pin 130, and a guide pin 130 is rotatable to allow the needle 62 to pitch relative to the longitudinal axis A as the needle 62 moves axially, for example as the needle 62 moves into engagement with the distal end 64.

The neck 114 extends between the proximal end portion 112 and the distal end 64 and defines a throat 132. The needle 62 is movable from the proximal end portion 112, out of the needle exit port 123, across the throat 132, and into a cavity 134 formed in the distal end 64. In one embodiment, the distal end 64 and the cavity 134 are both radially spaced away from the longitudinal axis A, and the guide pin 130 rotates to enable the needle 62 to move out of the needle exit port 123, pitch upwards, and into the cavity 134. In one embodiment, a top surface of the neck 114 defines an open, exposed groove configured to receive and guide at least the suture 42 that extends from the capsule 40 back to the handle 52 (FIG. 1A).

As described below, the cavity 134 is configured to retain the capsule 40 attached to the first suture 42 (FIG. 1B), and the needle 62 is configured to penetrate tissue and enter a cavity 134, frictionally engage the capsule 40 and the suture 44, and pull the capsule 40 and the sutures 42, 44 through the tissue and into the needle exit port 123.

As described below, embodiments of the head 56 include mechanisms configured to linearly direct the needle 62 out of the needle exit port 123 across the throat 132 and into the cavity 134 for engagement with the capsule 40. Other embodiments of the head 56 include mechanisms configured to shunt the needle 62 (e.g., pitch the needle 62 upward relative to the axis A away from the needle exit port 123 and into the cavity 134 for engagement with the capsule 40).

Figure 4:
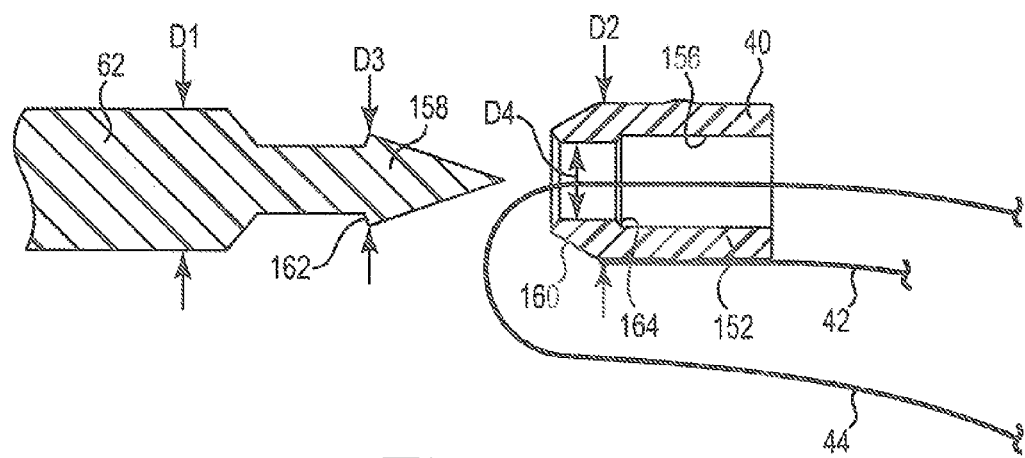
FIG. 4 is a cross-sectional view of the needle illustrated in FIG. 3 aligned for engagement with the suturing capsule.

FIG. 4 is a side view of the needle 62 aligned for engagement with the capsule 40 and the sutures 42, 44. The needle 62 is preferably machined from metal such as stainless steel or a shape memory alloy such as NITINOL (Nickel Titanium Naval Ordinance Laboratory), as examples. In one embodiment, the capsule 40 is a tubular capsule that is molded from plastic to integrally capture/bond with the first suture 42. Suitable plastic materials for fabricating the capsule 40 include polypropylene, polysulfone, urethane, or polyetherimide as examples. The suture 42 includes polypropylene suture, monofilament suture, braided suture, coated suture materials or the like, as examples.

The capsule 40 is sized to be deposited and retained in the cavity 134 (FIG. 3) and defines a recess 156 or tubular hole 156 that is configured to receive the second suture 44. The recess 156 formed in the capsule 40 is sized to engage with a leading end 158 of the needle 62. In one embodiment, the needle 62 is shaped to promote secure engagement with a capsule 40 and the leading end 158 is formed to have a conical point with a shoulder 162 that is sized to be pressed into engagement with a flange 164 of the recess 156. For example, the flange 164 is shaped and sized to accommodate the second suture 44 and to frictionally engage (e.g., snap-fit) in a "locked" manner with a shoulder 162 of the needle 62 as the needle 62 is driven into the recess 156. The capsule 40 is configured to be detached from the needle 62 by the guide pin 130 (FIG. 3) after the needle 62 pulls the capsule 40 rearward in a proximal direction into the head 56.

The conical point of the needle 62 is configured to form a channel when advanced through tissue, and the capsule 40 is sized to be pulled through the channel in the tissue made by the needle 62. In one embodiment, the leading end 160 of the capsule 40 is chamfered and the needle 62 is configured to draw the chamfered (or truncated) end 160 of the capsule 40 first through the tissue. In one embodiment, the leading end 160 of the capsule 40 is a blunt end similar to that illustrated for the trailing end of the capsule 40, and the needle 62 is configured to draw the blunt end 160 of the capsule 40 blunt end-first through the tissue.

For example, in one embodiment the needle 62 has a first diameter D1 and the capsule 40 has a diameter D2, were the diameter D1 is equal to or greater than the diameter D2. In this manner, the capsule 40 is sized to follow the needle 62 and be retracted through the channel formed in the tissue by the needle 62.

The leading end 158 of the needle 62 is sized to frictionally engage with the recess 156 formed in the capsule 40. For example, in one embodiment the leading end 158 has a diameter D3 that is slightly greater than a diameter D4 formed in an opening of the recess 156. In this manner, when the leading end 158 of the needle 62 is inserted into the recess 156, the leading end 158 is forced into and seats within and captures the capsule 40.

FIGS. 5A-5H are schematic sectional views illustrating the suturing system 30 employed to throw the needle 62 from a proximal location to a distal location of the head 56, engage the needle 62 with the capsule 40 and the sutures 42, 44, and retract the capsule 40 in the sutures 42, 44 through tissue.

Figure 5A:
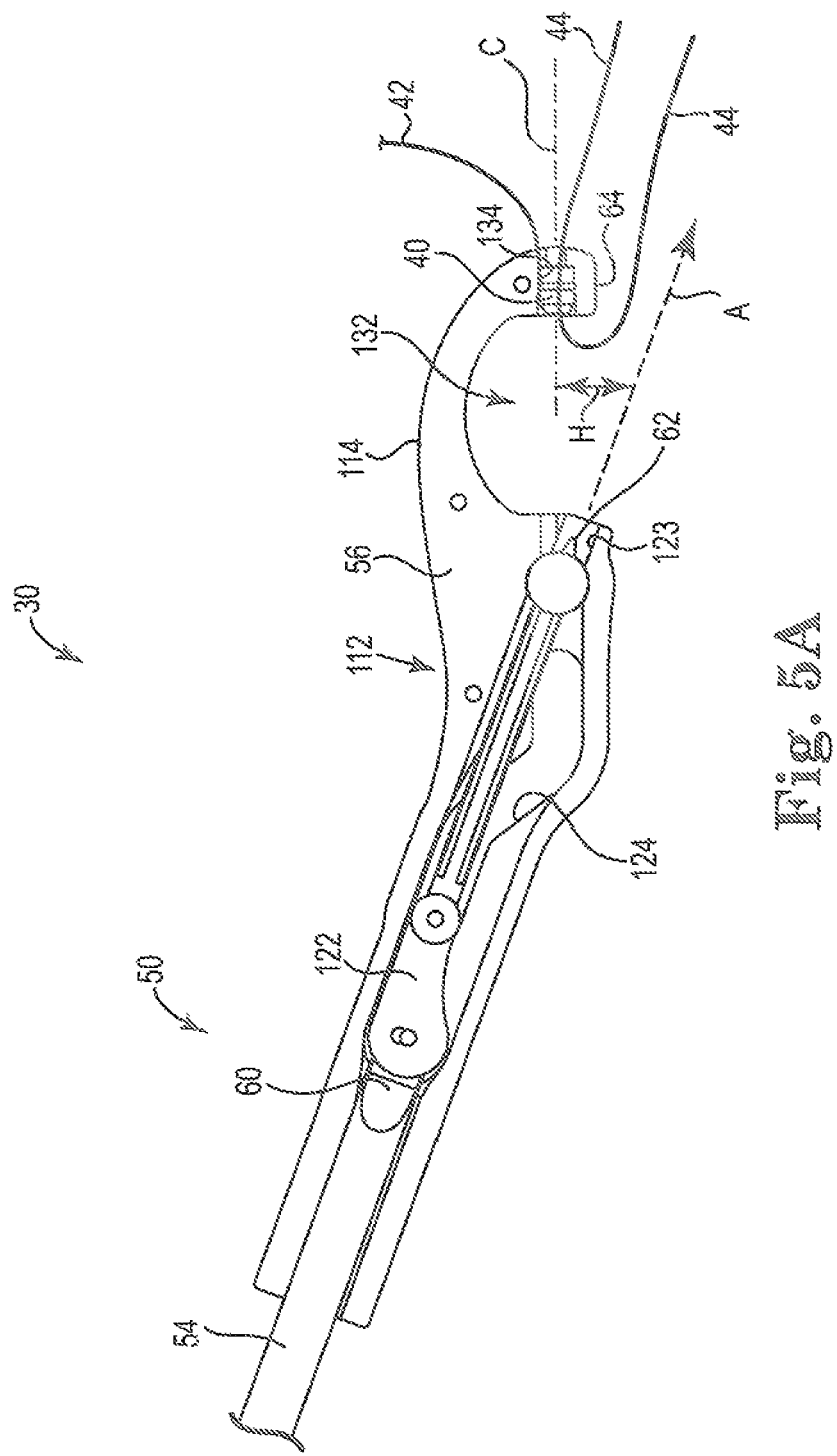
FIG. 5A is a schematic sectional view of one embodiment of the head of the tool illustrated in FIG. 1 engaged with tissue and the needle retracted within a proximal end portion of the head.

FIG. 5A is a schematic sectional view of system 30 with the needle 62 retracted into the needle exit port 123 and the capsule 40 loaded into the head 56. The capsule 40 is seated in the cavity 134 with both of the sutures 42, 44 trailing distal relative to the head 56. For example, the suture 42 is durably connected to the capsule 40 and the suture 44 is inserted through the recess 156 (FIG. 4) formed in the capsule 40. In one embodiment, distal end 64 includes a slot configured to enable the sutures 42, 44 to slide through the distal end 64 to facilitate loading the capsule 40 into the cavity 134. In one embodiment, the rod 60 and the needle 62 are aligned on the axis A when the needle 62 is retracted into the proximal end portion 112 as illustrated, and the capsule 40 is aligned on an axis C that is offset from the axis A by a distance H and is not aligned with the axis A.

FIG. 5B is a schematic sectional view of the system 30 with the head 56 engaged with tissue T. The throat 132 is placed onto the tissue T, for example a ligament or a muscle, and the needle 62 is positioned to pierce the tissue T.

Activating the actuator 58 (FIG. 1A) moves the rod 60 axially in a distal direction that directs the needle 62 out of the needle exit port 123 in a first direction along the axis A. In one embodiment, the pathway of the needle 62 exiting the needle exit port 123 is offset radially from the cavity 134. A portion of the needle 62 extends from the needle exit port 123 partway across the throat 132, and the guide pin 130 is configured to rotate counter-clockwise to allow the movement of the link 122 within the trace 124 to shunt the leading end 158 of the needle 62 to a direction aligned with the cavity 134. Additional activation of the actuator 58 drives the needle 62 through the tissue T to form a channel in the tissue T. Complete activation of the actuator 58 drives the needle 62 into engagement with the capsule 40 and the sutures 42, 44.

FIG. 5C is a schematic sectional view of the needle 62 engaged with the capsule 40 and the sutures 42, 44. The needle 62 has penetrated the tissue T and formed a channel 170 in the tissue P. The second suture 44 flexes or bends around the shoulder 162 (FIG. 4) of the needle 62 when the needle 62 is engaged with the capsule 40. In this configuration, the needle 62 is frictionally engaged with both the capsule 40 and the suture 44. Thus, in one embodiment the first suture 42 is durably connected to the capsule 40 and the second suture 44 is removably inserted into the through-hole recess 156 of the capsule 40 and frictionally coupled to the capsule 40 by the needle 62.

Figure 5D:
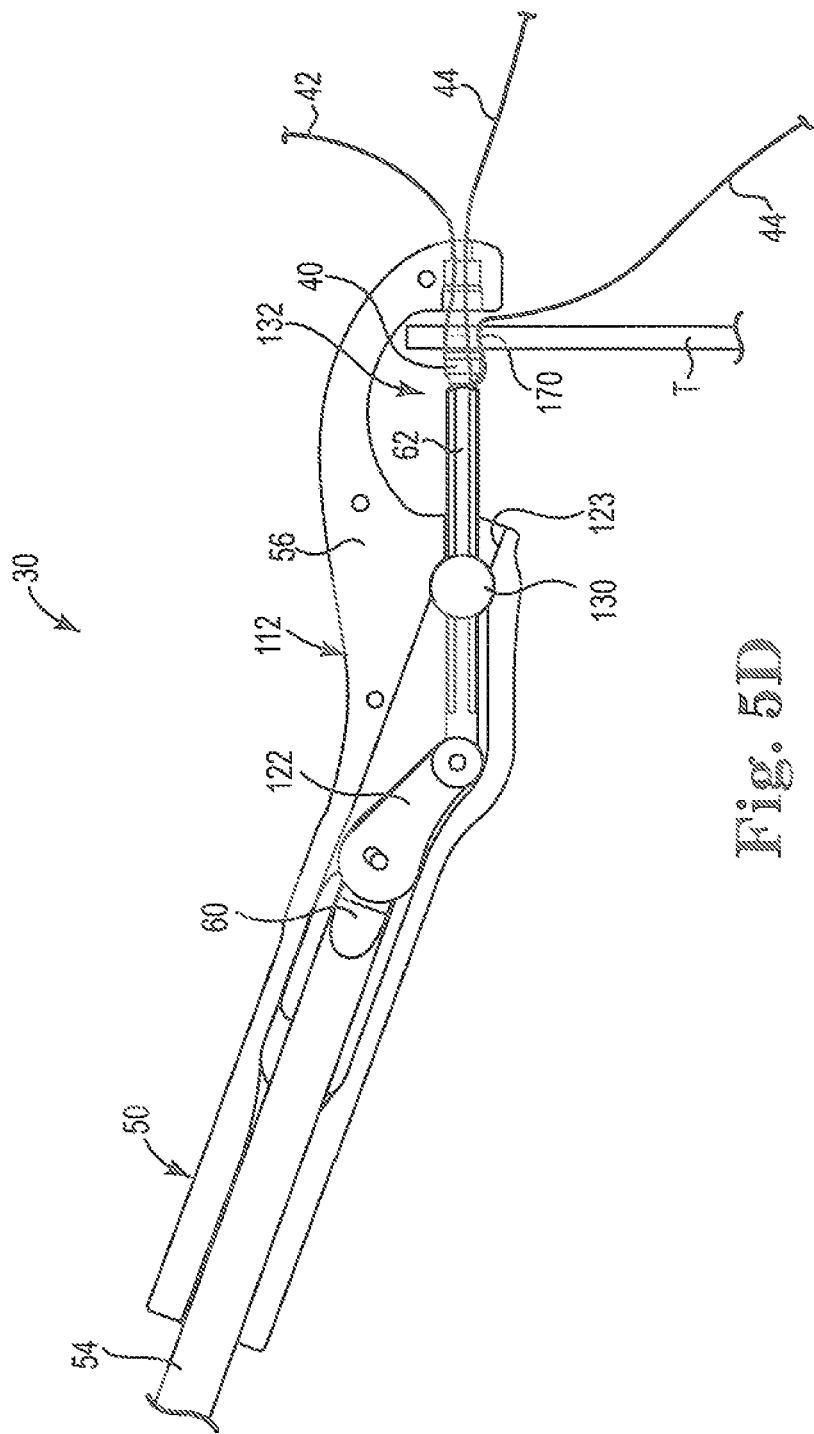
FIGS. 5D-5F are schematic sectional views of the needle engaged with the capsule and retracting multiple lines of suture through the tissue.

FIG. 5D is a schematic sectional view of the needle 62 engaged with the capsule 40 and pulling the capsule 40 and the sutures 42, 44 through the channel 170 formed in the tissue T. In one embodiment, the surgeon positions both ends of the second suture 44 to trail away from the distal end 64 of the head 56, which results in a double thickness of the suture 44 being drawn through the channel 170 formed in the tissue T. Thus, the sutures 42, 44 both trail through the channel 170 formed in the tissue T and out of a backside of the cavity 134.

Figure 5E:
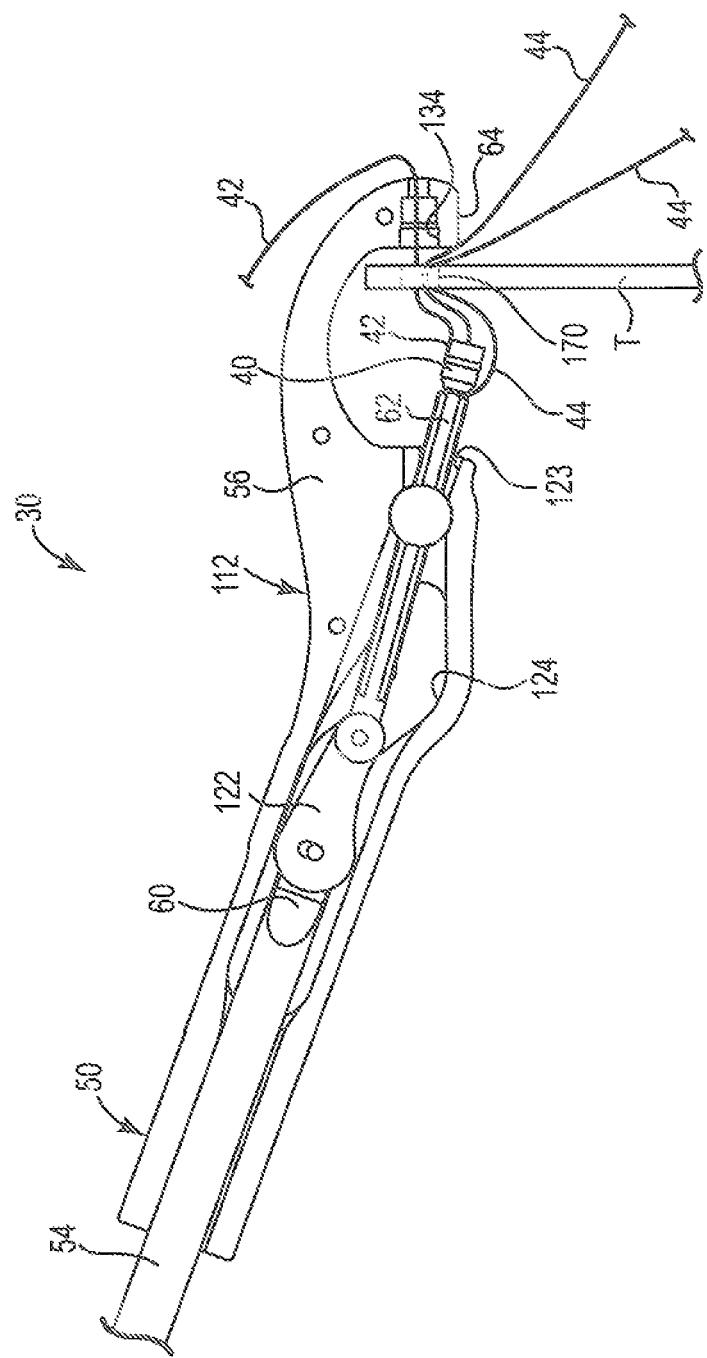

FIG. 5E is a schematic sectional view of the needle 62 returning to the needle exit port 123. The capsule 40 and the sutures 42, 44 are pulled through the tissue T to stitch or throw multiple lines of suture through tissue.

Figure 5F:
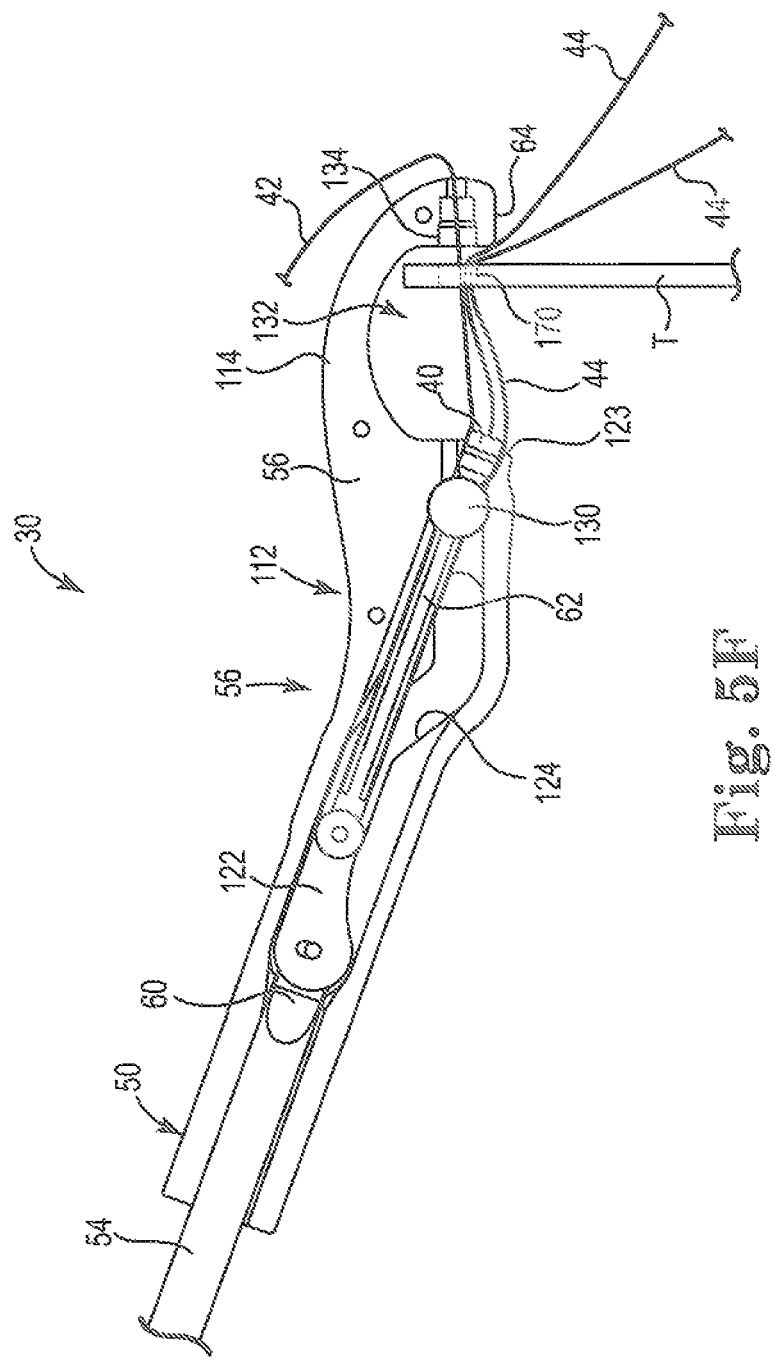

FIG. 5F is a schematic view of the needle 62 retracted into the head 56 with the capsule 40 parked in the needle exit port 123. The sutures 42, 44 trail through the channel 170 formed in the tissue T. The tool 50 is now positioned to be separated from the tissue T leaving the sutures 42, 44 secured to the tissue T through the channel 170.

In one embodiment, the needle exit port 123 is sized to receive the capsule 40 such that the port 123 forms a capsule garage 123 into which the capsule 40 is parked after extraction from the cavity 134. The rod 60 has drawn the link 122 into full rearward engagement with the trace 124 such that the needle 62 is retracted into the head 56. The capsule 40 is parked inside the needle exit port 123 and the sutures 42, 44 extend across the throat 132, which provides the surgeon with access to the capsule 40 and guidance and control of the suture lines 42, 44.

In one embodiment, and as described above with reference to FIG. 2, the knob 80 is configured to be turned to incrementally retract the rod 60 an additional distance into the handle 52, which separates the needle 62 from the capsule 40 that is parked in the needle exit port 123. The additional retraction of the needle 62 by the rearward motion of the rod 60 causes the capsule 40 to be pressed against the guide pin 130, which shears the capsule 40 off of the needle 62.

Figure 5G:
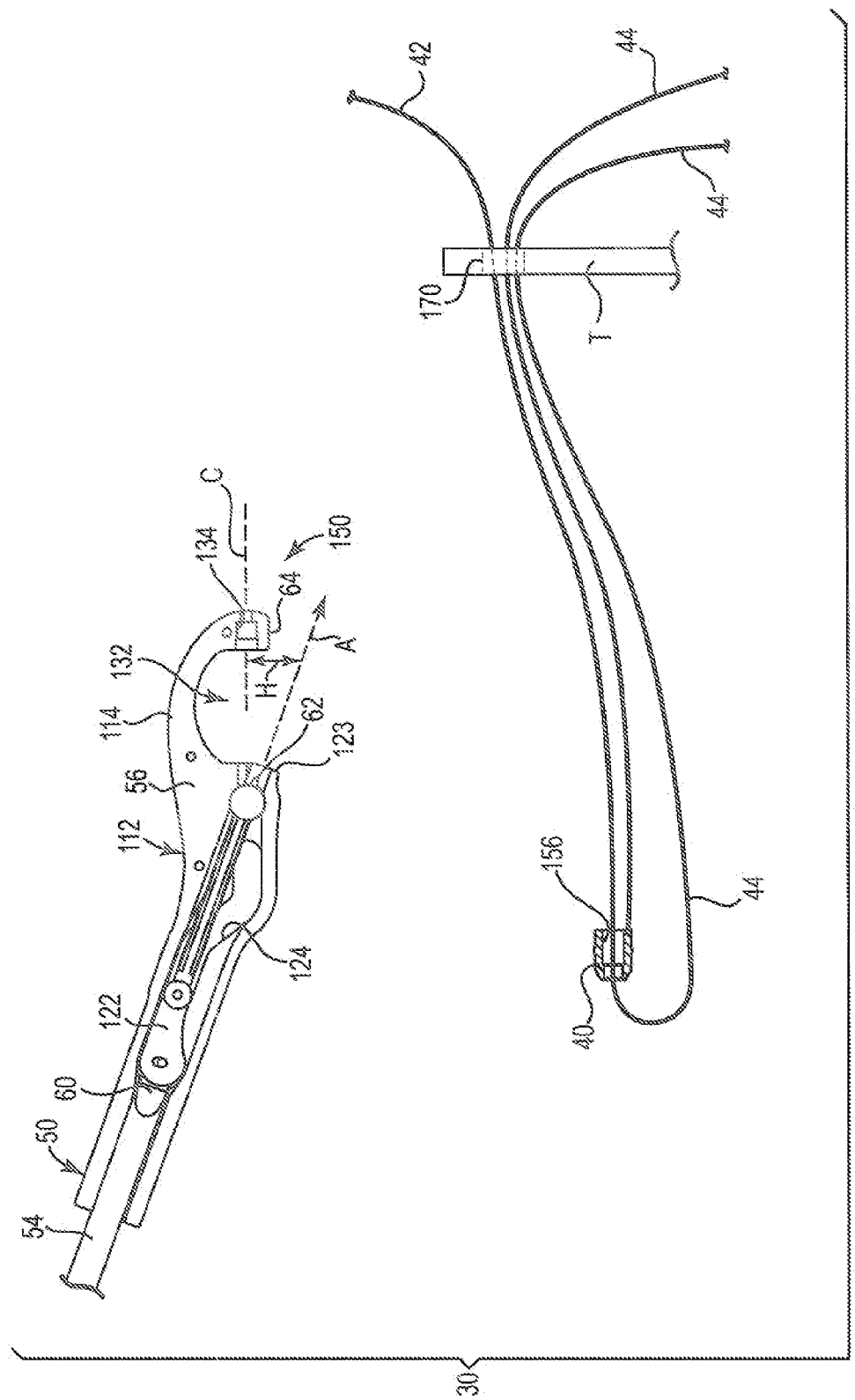
FIG. 5G is a side schematic view of the head of the tool disengaged from the tissue and the capsule, with the capsule retaining the multiple lines of suture.

FIG. 5G is a side view of the sutures 42, 44 sutured into the tissue T. The capsule 40 has been ejected from the head 56. In one embodiment, the capsule 40 and the suture 42 are both sacrificial components that are cut or otherwise removed from the suture 44. For example, in one embodiment the suture 42 is cut with a scissors and the capsule 40 is moved along the suture 44 to allow both the capsule 40 and the suture 42 to be discarded.

Figure 5H:
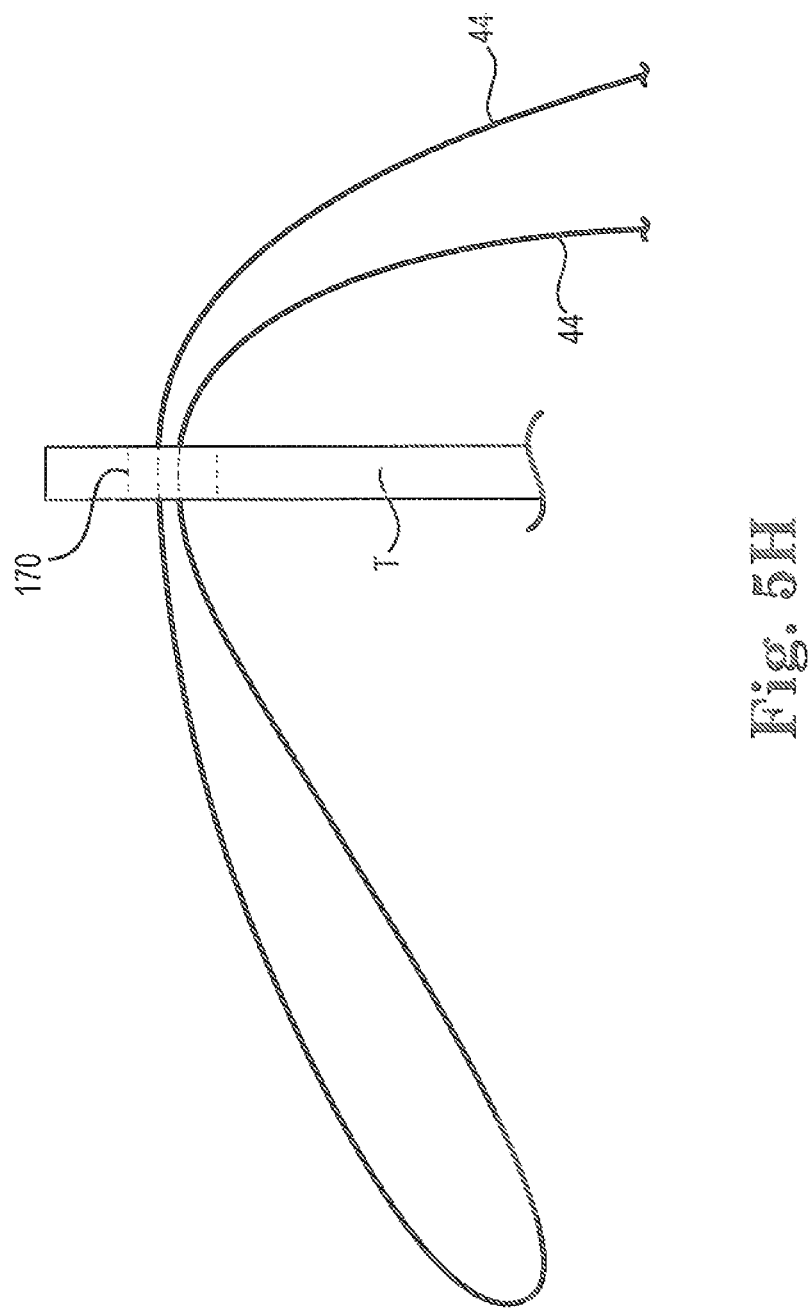
FIG. 5H is a side schematic view of one embodiment showing one line of suture stitched into the tissue after the capsule and its suture have been removed and discarded.

FIG. 5H is a side view of the suture 44 sutured into the tissue T. With additional reference to FIG. 5D, a double thickness of the suture 44 is drawn through the channel 170 formed in the tissue T when both ends of the second suture 44 are positioned to trail away from the distal end 64 of the head 56. Other embodiments described below provide for the system 30 to place a single thickness of the suture 44 through the channel 170 formed in the tissue T.

In one embodiment, the tissue T is located within the pelvis of the patient and the head 56 (FIG. 5G) accesses the tissue T through a blind passage. Thus, the surgeon throws the sutures 42, 44 through tissue T by "feel" by manipulating the handle 52 (FIG. 1A) without viewing the head 56. The head 56 is removed from the pelvis after the sutures 42, 44 are thrown through the tissue T. Typically the capsule 40 and the suture 42 are both removed and discarded leaving the suture 44 sutured through the tissue T. The suture 44 is provided to secure support fabric or other material to the tissue T.

FIGS. 6A-6D illustrate another embodiment of the system 30 employed to place a single thickness of the suture 44 through the tissue T.

FIG. 6A is a schematic sectional view of the head 56 of the tool 50 engaged with the tissue T. The capsule 40 is loaded into the cavity 134 and the suture 42 trails away from the distal end 64, preferably back to the handle 52 (FIG. 1A). The alternate second suture 44 is threaded through the recess 156 (FIG. 4) of the capsule 40 such that the right-hand end of the suture 44 trails in a distal direction to the right, and a left and end of the suture 44 trails in front of or around the tissue T in a proximal direction relative to the head 56.

Figure 6B:
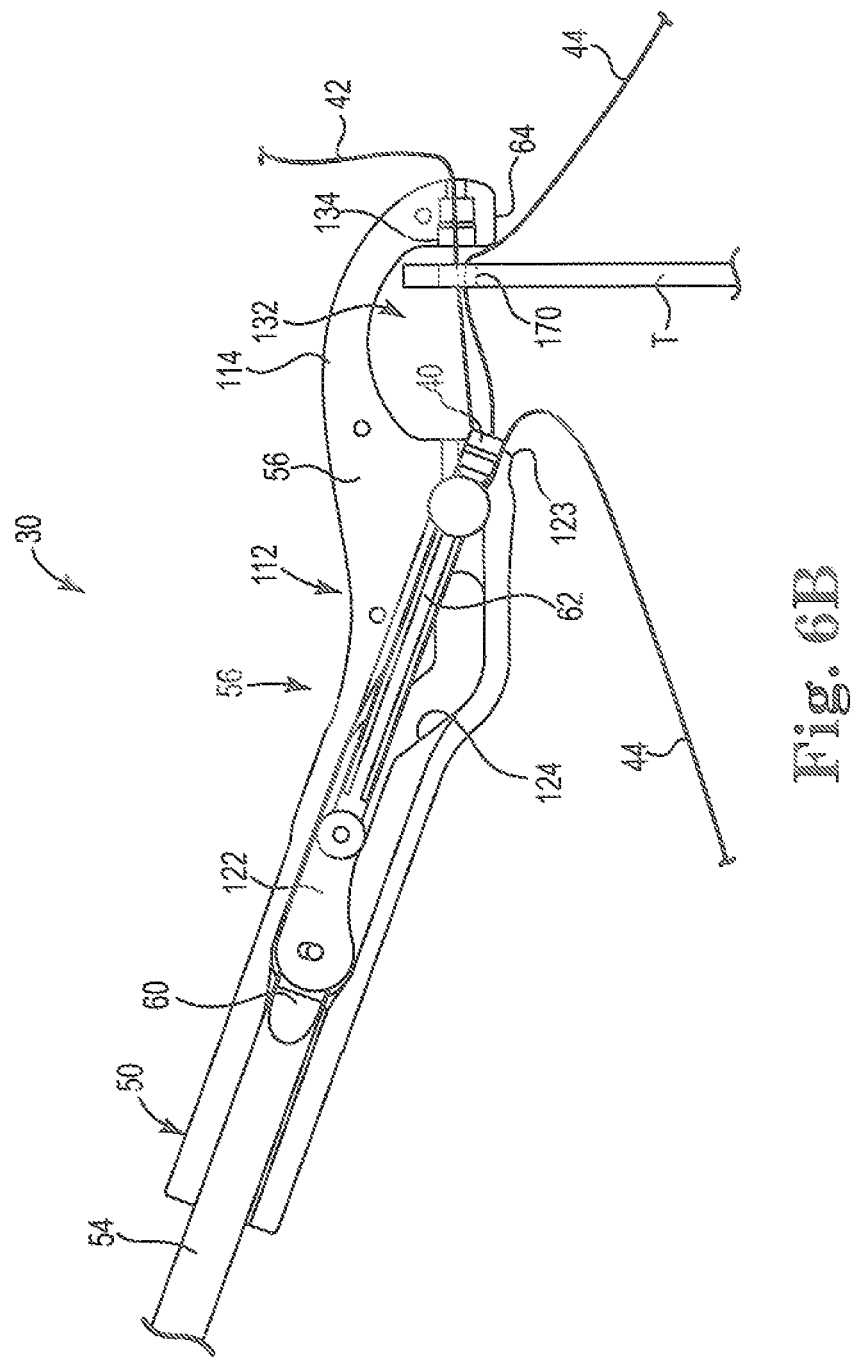

FIG. 6B is a schematic sectional view of the needle 62 engaged with the capsule 40 and the alternate second suture 44. The capsule 40 is retracted through the tissue T back into the needle exit port 123. The suture 42 is connected to the capsule 40 and trails through the channel that is formed in the tissue T in a distal direction. The alternate second suture 44 trails through the channel formed in the tissue T and includes an end on each side of the tissue T.

Figure 6C:
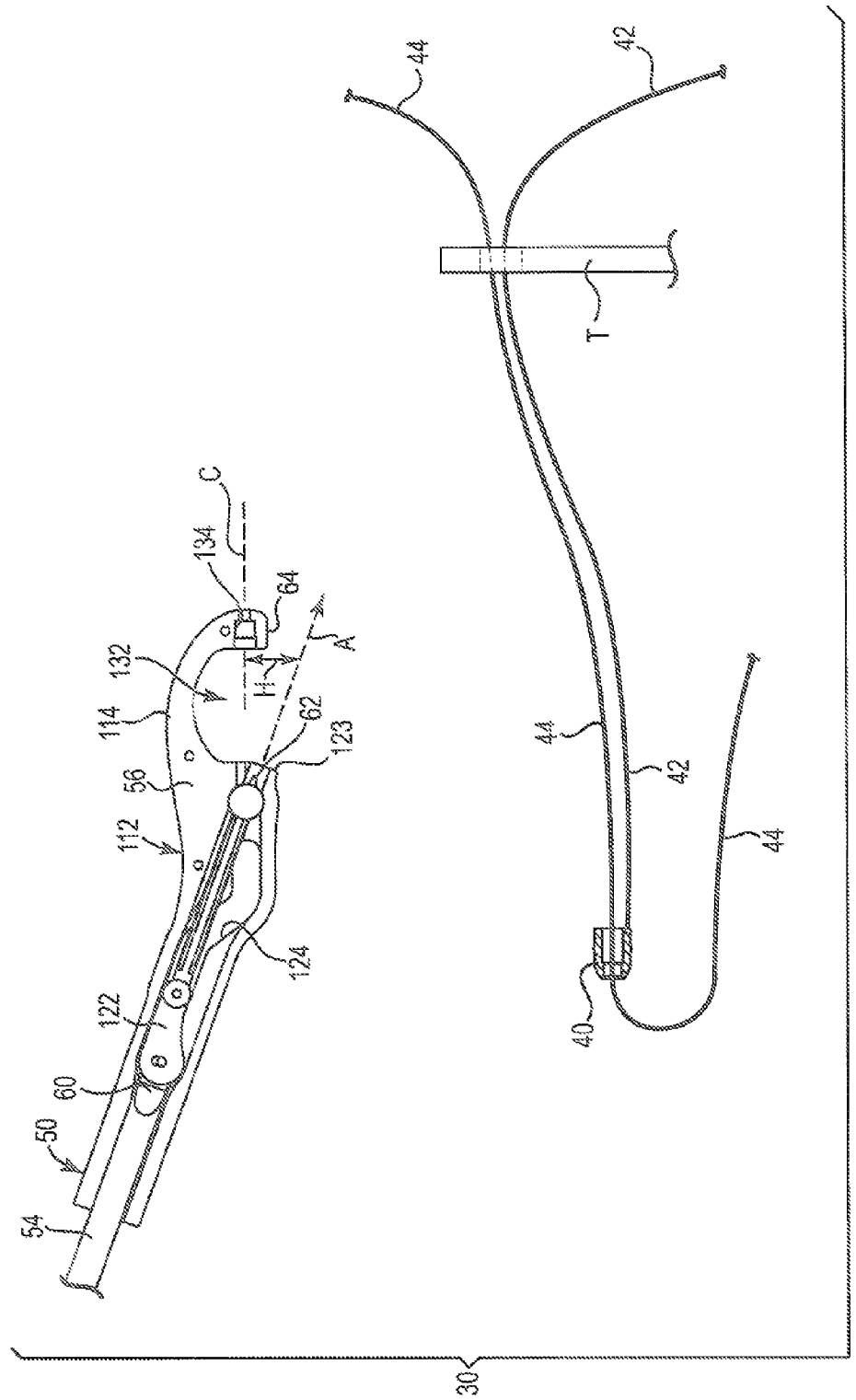

FIG. 6C is a schematic sectional view of the head 56 of the tool 50 separated from the tissue T with the capsule 40 disengaged from the needle 62. The suture 42 that is connected to the capsule 40 trails through the channel 170 that is formed in the tissue T. The alternate second suture 44 likewise trails through the channel 170 in the tissue T and includes an end on each side of the tissue T. In this configuration, the suture 42 is cut or severed and pulled out of the channel 170 and the capsule 40 is directed along the suture 44, removed and discarded, leaving the alternate second suture 44 sutured through the tissue T. In one embodiment, the suture 42 is a sacrificial polypropylene suture and a suture 44 is a bioabsorbable or body absorbable suture.

Figure 6D:
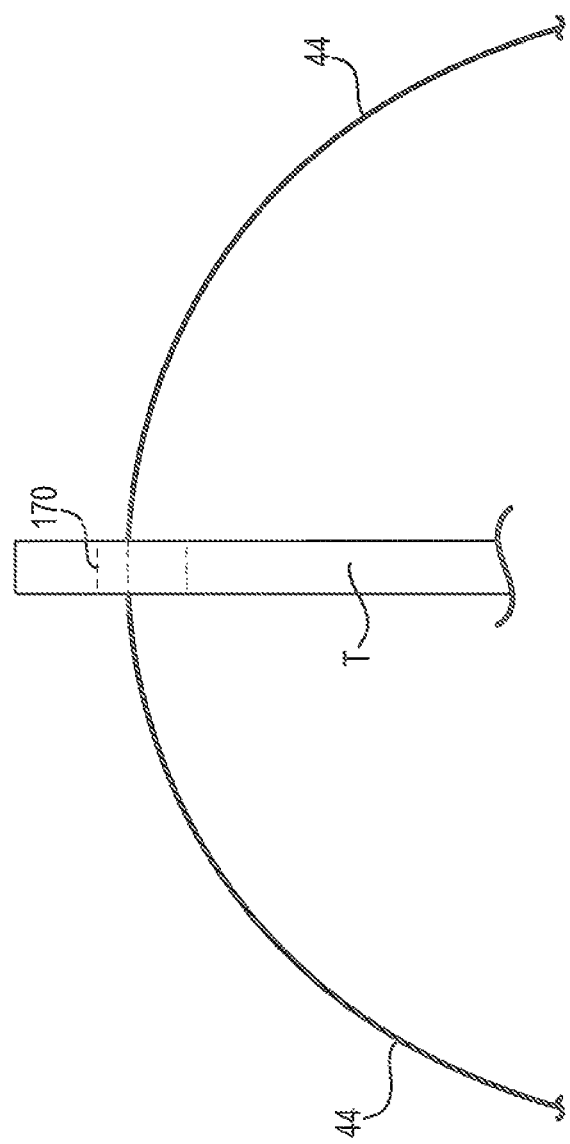

FIG. 6D is a schematic sectional view of the alternate second suture 44 stitched through the tissue T. In one embodiment, the tissue T is located inside the pelvis and both ends of the second suture 44 are directed to a location outside of the body of the patient. For example, the suture 44 is suitably secured to a surface of a surgical drape that is placed over the patient. In this manner, the suture 44 provides a pathway into the pelvis for the attachment of support material to the tissue T of the pelvis.

Figure 7:
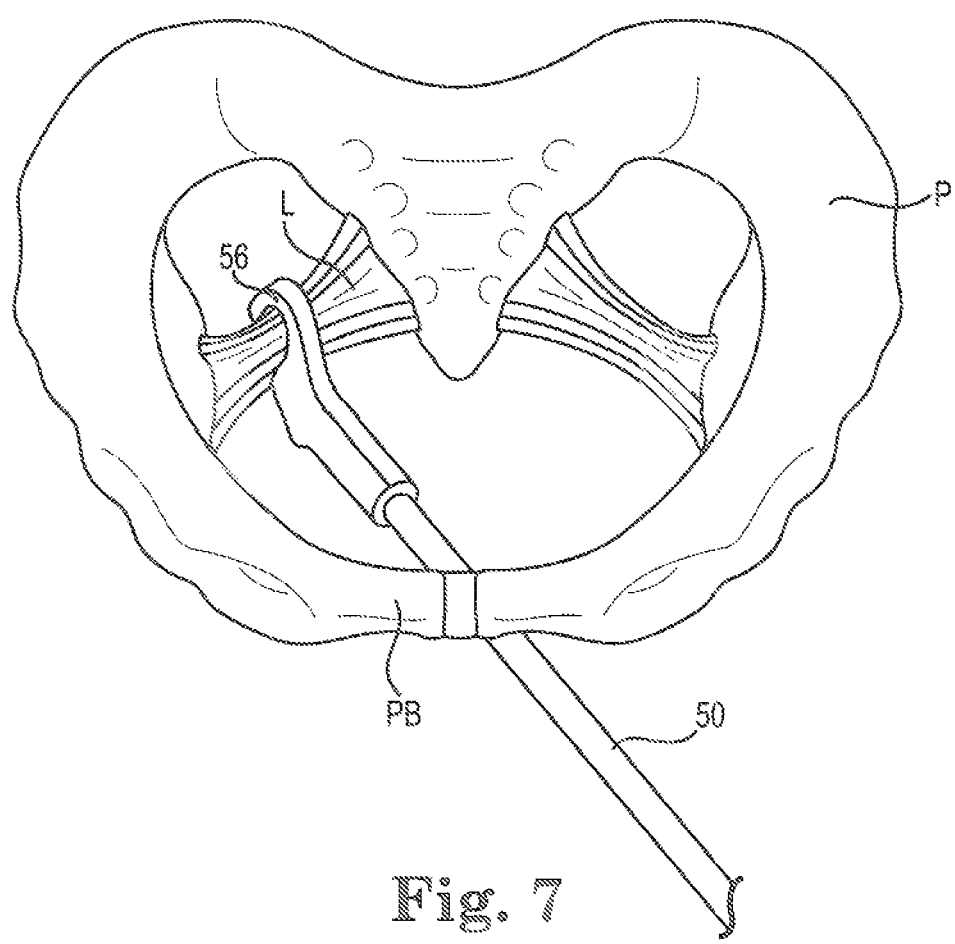
FIG. 7 is a perspective view of one embodiment of the tool illustrated in FIG. 1 placing multiple lines of suture in tissue within a pelvis accessed via a blind passage.

FIG. 7 is a schematic view of the tool 50 engaged with a ligament L inside of a pelvis P via a blind passage caudad the pubic bone PB. For example, in one embodiment the head 56 is sized for insertion through a vaginal incision into the pelvic cavity to allow the head 56 of the tool 50 to access the sacrospinous ligament. The tool 50 is operated to throw the sutures 42, 44 through the ligament, as described above. In one embodiment, a support fabric is attached to a ligament L with multiple individual suture lines 44 that are sutured to multiple target landmarks within the pelvis P. Each one of the multiple suture lines 44 is thrown through a suitable landmark as identified by the surgeon and organized such that the ends of the suture 44 are available outside of the pelvis P for the delivery of the support fabric back along the suture lines 44 into the pelvis P.

Figure 8:
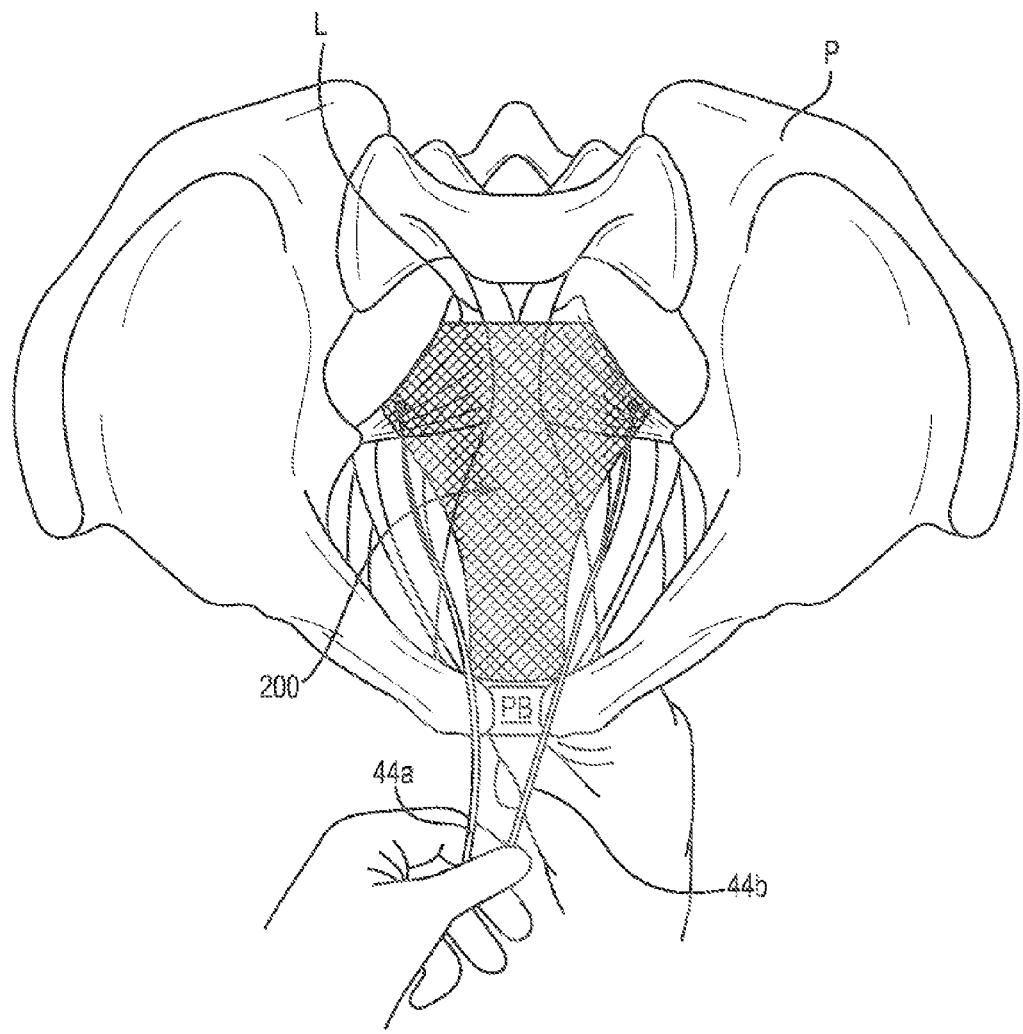
FIG. 8 is a perspective view of the pelvis with a support fabric attached to tissue of the pelvis and retained by the multiple lines of suture delivered by the tool illustrated in FIG. 1.

FIG. 8 is a perspective schematic view of support fabric 200 attached to a landmark such as the sacrospinous ligament L by multiple separate suture lines 44. In one embodiment, multiple separate suture lines 44a and 44b are attached to a suitable landmark in the pelvis P and the suture lines 44a and 44b are extended outside of the pelvis P for access by the surgeon. The support fabric 200 is attached to a first one of the suture lines 44a, a knot is formed in the suture line 44a, and the support fabric 200 is delivered along the suture line 44a into the pelvis P to the landmark. This procedure is repeated with regard to the suture line 44b and a second location of the support fabric 200 is attached to a second landmark within the pelvis P. Multiple other suture lines 44 may be placed according to the procedure described above to anchor additional portions of the support fabric 200 traditional landmarks within the pelvis P.

Suitable support fabric 200 includes autograft material (the patient's own tissue), allograft material (tissue from a cadaver), xenograft material (tissue from another species), or synthetic materials such as woven fabrics, meshes formed of one or more strand materials, nonwoven fabrics, meshes formed from polypropylene, fibrillated fibers, or spun and fibrillated fibers that are provided with voids (pores) configured to allow tissue ingrowth into the fabric 200. The pores are generally larger, on average, than 75 μm.

Consistent with the description of the surgical procedure described above, embodiments of the system 30 allow for suturing tissue by driving a needle from a tool through tissue to form a channel in the tissue; inserting the needle into a capsule that is connected to a first length of suture attached to the capsule; engaging the needle with one or more second lengths of suture inserted through the capsule; and pulling both the first length of suture and the second length(s) of suture through the channel formed in the tissue.

The system facilitates a method of suturing tissue that includes forming an incision; inserting the tool into the incision and accessing the tissue with the tool through a blind passage; and retrieving both the first length of suture and the second length of suture through the channel formed in the tissue to a location exterior the incision. This method includes accessing tissue interior the pelvis by passing the tool through the incision, driving the needle through a ligament, and guiding both the first length of suture and the second length of suture through the channel formed in the ligament to a location exterior the pelvis. The method further includes cutting the first length of suture attached to the capsule; disengaging the capsule from the second length of suture; and retaining two opposed ends of the second length of suture in the location exterior the pelvis. The method further includes attaching a support fabric to the second length of suture. The method further includes tying a knot in the second length of suture and securing the support fabric to the second length of suture. The method further includes transporting the support fabric along the second length of suture to the ligament and thus securing the support fabric to a landmark within the pelvis.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A suturing system comprising:
    a tool comprising a head having a proximal portion housing a needle movable through a needle exit port of the head and a distal end spaced apart from the proximal portion by a throat, where the distal end of the head is radially offset from the longitudinal axis and defines a cavity;
    a first suture attached to a capsule, the capsule sized for placement in the cavity, the capsule defining a through-hole sized for engagement with the needle; and
    a second suture configured to be threaded through the through-hole of the capsule;
    wherein the needle is movable from the proximal portion of the head across the throat to form a channel in tissue, and retractable into the needle exit port to draw the capsule and the first and second sutures through the channel formed in the tissue to place multiple lengths of suture in the tissue;
    wherein the first suture is molded to ca sole second suture is removably inserted into the through-hole of the capsule and adapted to be frictionally coupled to the capsule by the needle.

2. The suturing system of claim 1, wherein the tool comprises a handle having an actuator, the handle connected with the head by a shaft and the actuator connected with the needle by a rod that passes through the shaft.

3. The suturing system of claim 2, wherein the shaft is a malleable and bendable shaft.

4. The suturing system of claim 1, wherein the head is sized for insertion into a pelvic cavity through a vaginal incision and each of the multiple lengths of suture is greater than 2 inches.

5. The suturing system of claim 1, wherein the head is sized for insertion into a pelvic cavity through a vaginal incision and each of the multiple lengths of suture is greater than 4 inches.

6. The suturing system of claim 1, wherein the head is sized for insertion into a pelvic cavity through a vaginal incision and each of the multiple lengths of suture is greater than 8 inches.

7. The suturing system of claim 1, wherein the first suture is a polypropylene suture and the second suture is not a polypropylene suture.

8. The suturing system of claim 1, wherein the first suture is a polypropylene suture and the second suture is a bioabsorbable suture.

9. The suturing system of claim 1, wherein the first suture is a polypropylene suture and the second suture is a polyglycaprone suture.

10. The suturing system of claim 1, wherein the first suture is a polypropylene suture and the second suture is a polyglactin suture.

11. The suturing system of claim 1, wherein the first suture is a polypropylene suture and the second suture is a polydioxanone suture.

12. The suturing system of claim 1, wherein the first suture is a polypropylene suture and the second suture is a body-absorbable suture.

* * * * *

UNITED STATES PATENT AND TRADEMARK OFFICE
CERTIFICATE OF CORRECTION

| | | |
|---|---|---|
| PATENT NO. | : 8,623,033 B2 | Page 1 of 1 |
| APPLICATION NO. | : 13/414738 | |
| DATED | : January 7, 2014 | |
| INVENTOR(S) | : Thomas Kubalak | |

It is certified that error appears in the above-identified patent and that said Letters Patent is hereby corrected as shown below:

In the claims

Col. 11, at Claim 1, line 35 "ca sole" should read --capsule--.

Signed and Sealed this
Second Day of September, 2014

Michelle K. Lee
*Deputy Director of the United States Patent and Trademark Office*